(12) United States Patent
Tsuji et al.

(10) Patent No.: US 8,927,284 B2
(45) Date of Patent: Jan. 6, 2015

(54) METHOD FOR PRODUCING TOOTH

(75) Inventors: Takashi Tsuji, Chiba (JP); Kazuhisa Nakao, Chuohon-Cho (JP)

(73) Assignee: Organ Technologies, Inc., Tokyo (JP)

( * ) Notice: Subject to any disclaimer, the term of this patent is extended or adjusted under 35 U.S.C. 154(b) by 0 days.

(21) Appl. No.: 13/146,029

(22) PCT Filed: Jan. 14, 2010

(86) PCT No.: PCT/JP2010/000180
§ 371 (c)(1),
(2), (4) Date: Aug. 31, 2011

(87) PCT Pub. No.: WO2010/087118
PCT Pub. Date: Aug. 5, 2010

(65) Prior Publication Data
US 2011/0306135 A1  Dec. 15, 2011

(30) Foreign Application Priority Data

Jan. 28, 2009  (JP) ................................. 2009-017387

(51) Int. Cl.
*C12N 5/02* (2006.01)
*A61L 27/38* (2006.01)

(52) U.S. Cl.
CPC ......... *A61L 27/3886* (2013.01); *A61L 27/3804* (2013.01); *A61L 27/3865* (2013.01)
USPC .......................................... 435/395; 435/325

(58) Field of Classification Search
CPC ........... A61K 2300/00; A61K 38/1875; A61K 35/32; A61K 35/28; A61K 6/02; C12N 5/0654; C12N 2502/1364; C12N 5/0664; A61L 27/3813; A61C 8/0006; A61C 8/0018; A61C 13/08
See application file for complete search history.

(56) References Cited

U.S. PATENT DOCUMENTS

| 6,276,939 B1 | 8/2001 | Shimizu et al. | |
| 2003/0235580 A1* | 12/2003 | Zhang | 424/130.1 |
| 2010/0021866 A1 | 1/2010 | Tsuji et al. | |
| 2010/0119997 A1 | 5/2010 | Tsuji et al. | |
| 2010/0129771 A1* | 5/2010 | Tsuji et al. | 433/172 |
| 2013/0109093 A1 | 5/2013 | Tsuji et al. | |

FOREIGN PATENT DOCUMENTS

| CN | 1279596 A | 1/2001 |
| CN | 101189033 A | 5/2008 |
| EP | 1905459 A1 | 4/2008 |
| JP | 2008-029756 A | 2/2008 |
| JP | 2008-029757 A | 2/2008 |
| JP | 2008-126005 A | 6/2008 |
| JP | 2008-200033 A | 9/2008 |
| JP | 2008-206500 A | 9/2008 |
| WO | 2006/020240 A2 | 2/2006 |
| WO | 2006/129672 A1 | 12/2006 |

OTHER PUBLICATIONS

Nakao, Kazuhisa, et al., "Regulations of size and shape of the bioengineered tooth by a cell manipulation method"; 2009 International Sympsoium on Micro- NanoMechatronics and Human Science (online at http://ieeexplore.ieee.org); ISBN: 978-1-4244-5095-4/09, pp. 123-125.*
Honda, Masaki, et al., "The sequential seeding of epithelial and mesenchymal cells for tissue-engineered tooth regeneration"; Biomaterials 28 (2007) pp. 680-689 (online at http://sciencedirect.com).*
Thesleff, Irma, et al., "Cell-matrix interactions in tooth development"; International Journal of Developmental Biology 33 (1989) pp. 91-97 (online at http://www.ijdb.ehu.es).*
Bobis, Sylwia, et al., "Mesenchymal Stem cells: characteristics and clinical applications"; Folia Histochemica Et cytobiologica 44, 4 (2006) pp. 215-230 (online at http://fhc.amb.edu.pl).*
Mitssiadis, Thimios A, et al., "Development of teeth in chick embryos after mouse neural crest transplantations"; Proceedings of the National Academy of Sciences (PNAS) 100,11 (2003) pp. 6541-6545 (online at pnas.org).*
Honda, Masaki et al., "Tooth forming potential in embryonic and postnatal tooth bud cells"; Medical Molecular Morphology (2008) 41:183-192.*
Hillson, Simon et al., Alternative Dental Measurements: Proposals and Relationships with Other Measurements (2005) 126:413-426.*
Glossary of Biotechnology and Genetic Engineering (Cell aggregate definition).*
Nakao et al. "The development of a bioengineered organ germ method." Nature Methods , 4, 227-230 2007.*
Nakao et al. "The development of a bioengineered organ germ method." Nature Methods , Supplementary 1, 2007.*
Nakao et al. "The development of a bioengineered organ germ method." Nature Methods , Supplementary 2, 2007.*
Nakao et al. "The development of a bioengineered organ germ method." Nature Methods , Supplementary 5, 2007.*
Wright et al. "Normal Formation and Development defects of the human dentition." Pediatric Oral Health, 2005, 47 (5): 975-1000.*
Markowicz et al. "Adult Bone Marrow Mesenchymal Stem Cells as Feeder Cells for Human Keratinocytes: New Approaches in Bilayered Skin Replacements." Chapter 4: Topics in Tissue Engineering, 2005, vol. 2. pp. 2-12.*
Wang et al. "Induction of human keratinocytes into enamel-secreting ameloblasts." Dev Biol. Aug. 15, 2010; 344(2): 795-799.*

(Continued)

*Primary Examiner* — Thaian N Ton
*Assistant Examiner* — Titilayo Moloye
(74) *Attorney, Agent, or Firm* — Osha Liang LLP

(57) ABSTRACT

A method for producing a tooth having a desired length in one direction includes the steps of: placing a first cell aggregate and a second cell aggregate in the inside of a support while bringing the first and the second cell aggregates into close contact with each other; and culturing the first and the second cell aggregates in the inside of the support, in which the first cell aggregate is composed of one of mesenchymal cells or epithelial cells and the second cell aggregate is composed of the other, and the size of the tooth is controlled by adjusting the length of contact between the first cell aggregate and the second cell aggregate in one direction.

14 Claims, 9 Drawing Sheets

(56) References Cited

OTHER PUBLICATIONS

Nakao et al. "The development of a bioengineered organ germ method." Nature Methods (2007); 4: pp. 227-230.*
Nakao et al. "The development of a bioengineered organ germ method." Nature Methods (2007); Supplemetal Fig. 1.*
Nakao et al. "The development of a bioengineered organ germ method." Nature Methods (2007); Supplemetal Fig. 2.*
Nakao et al. "The development of a bioengineered organ germ method." Nature Methods (2007); Supplemetal Fig. 5.*
Wright et al. "Normal Formation and Development defects of the human dentition" Pediatric Oral Healt (2005); 47 (5): pp. 975-1000.*
International Search Report w/translation from PCT/JP2010/000180 dated Apr. 6, 2010 (2 pages).
Espacenet English Abstract for Japanese Patent Publication No. JP 2008-126005, published Sep. 11, 2008 (1 page).
Hu, Bing, D.D.S., Ph.D., et al., "Tissue Engineering of Tooth Crown, Root, and Periodontium"; Tissue Engineering, vol. 12, No. 8, 2006, Mary Ann Lieert, Inc.; pp. 2069-2075.
Cai, Jinglei, et al., "Patterning the size and number of tooth and its cusps"; ScienceDirect (online at www.sciencedirect.com); Developmental Biology 304 (2007), Elsevier; pp. 499-507.
Espacenet English Abstract for International Patent Publication No. WO 2006-129672, published Dec. 7, 2006 (2 pages).
Espacenet English Abstract for Japanese Patent Publication No. JP 2008-029756, published Feb. 14, 2008 (1 page).
Espacenet English Abstract for Japanese Patent Publication No. JP 2008-200033, published Sep. 4, 2008 (1 page).
Espacenet English Abstract for Japanese Patent Publication No. JP 2008-029757 (1 page).
Espacenet English Abstract for Japanese Patent Publication No. JP 2008-206500, published Sep. 11, 2008 (1 page).
First Official Action dated Oct. 29, 2013, issued by the Japan Patent Office in related Japanese Patent Application No. 2010-548392 (3 pages).
Imamura, Hideo, et al., "Macrodontia of the Mandibular Left Second Premolar: A Case Report"; Dental Radiology 2003; vol. 43, No. 4; pp. 196-197, with English translation.
Notice of Reasons for Rejection (Office Action) dated Oct. 29, 2013, issued by the Japan Patent Office in corresponding Japanese Patent Application No. JP2010-548392, with English translation (7 pages).
Notice of Allowance dated Feb. 12, 2014, issued by the Japan Patent Office in corresponding Japanese Patent Application No. JP2010-548392, with English translation (6 pages).
English translation of a First Office Action issued Apr. 28, 2013, by The State Intellectual Property Office of The People's Republic of China in corresponding Chinese Patent Application No. CN-201080005943.3, (6 pages).
English translation of a Notice of Grant of Patent Right for Invention issued Dec. 17, 2013, by the Patent Office of the People's Republic of China in related Chinese Patent Application No. CN-201080005943.3 (2 pages).
Patent Examination Report No. 1 (Office Action) issued Sep. 11, 2013, by the Australian Patent Office in corresponding Australian Patent Application No. AU-2010209265 (3 pages).
Notice of Acceptance issued Jan. 3, 2014, by the Australian Patent Office in corresponding Australian Patent Application No. AU-2010209265 (2 pages).
Certificate of Grant of Patent dated Jan. 15, 2014, issued by The Registry of Patents Singapore, in corresponding Singapore Patent Application No. 201105200-8 (1 page).
Extended European Search Report dated Feb. 21, 2014, issued by the European Patent Office in corresponding European Patent Application No. EP-10735590.1 (6 pages).
English translation of an Official Action issued Sep. 11, 2013, by the Russian Patent Office in corresponding Russian Patent Application No. RU-2011135807 (3 pages).
Nakao, Kazuhisa, et al., "Regulations of size and shape of the bioengineered tooth by a cell manipulation method"; Micro-Nanomechatronics and Human Science, 2009, MHS 2009, International Symposium on, IEEE, Piscataway, NJ, USA; Nov. 9, 2009; XP031579599, ISBN: 978-1-4244-5094-7; pp. 123-126.
First Office Action dated Apr. 28, 2013, from the State Intellectual Property Office of The People's Republic of China in related Chinese Patent Application No. CN2010-80005943.3, with English translation (11 pages).
Espacenet English Abstract for Chinese Publication No. CN1279596, published Jan. 10, 2001 (2 pages).
Espacenet English Abstract for Chinese Publication No. CN101189033, published May 28, 2008 (2 pages).
Espacenet English Abstract for World International Patent Office (WIPO) Publication No. WO 2006/129672, published Dec. 7, 2006 (2 pages).
Espacenet English Abstract for Japanese Patent Publication No. JP 2008/126005, published Jun. 5, 2008 (2 pages).

* cited by examiner

Measured tooth crown region width

Measured tooth crown width

Bar : 500 μm

METHOD FOR PRODUCING TOOTH

TECHNICAL FIELD

The present invention relates to a method for producing a tooth having a desired size.

BACKGROUND ART

The tooth is an organ having enamel as its outermost layer, a hard tissue called dentin inside the layer, and furthermore, odontoblasts forming the dentin on the inner side with dental pulp in the center. Teeth may be lost due to tooth decay and periodontal disease, but because the presence of teeth has a big impact on one's appearance and on the taste of foods, the concern about tooth reproduction techniques has been increasing. Furthermore, concern towards about tooth reproduction techniques has also been increasing for reasons such as maintaining health and maintaining a high quality of life.

A tooth is a functional unit that is formed by the inducement of the generation process during the fetal period, and is formed by a plurality of cell species. A tooth is not generated by a stem cell system wherein cell species are generated from stem cells such as hematopoietic stem cells and mesenchymal stem cells in adults, and currently, teeth therefore cannot be regenerated with only transplantation of stem cells (stem cell transplantation) achieved by regenerative medicine. Although regeneration of teeth through identification of genes found specifically in the generation process of teeth and artificial inducement of a tooth germ has been examined, complete inducement of regeneration of teeth cannot be achieved only by identifying the genes.

Thus, in recent years, a method for obtaining regenerated teeth by reconstructing the tooth germ using an isolated tissue and cell derived from the tooth germ, and then transplanting the reconstructed tooth germ has been examined.

The present inventors figured out that by arranging a first cell mass and a second cell mass in contact with each other inside a support carrier made from collagen gel, wherein at least either the first cell mass is formed substantially from only one of either mesenchymal cells or epithelial cells derived from the tooth germ or the second cell mass is formed substantially from only the other type of cells, and then by culturing the first and the second cell mass inside the support carrier, cell differentiation can be induced effectively, and it is possible to produce a regenerated tooth germ and regenerated tooth having a specific cell arrangement and directionality (for example, see Patent Literature 1).

Furthermore, the present inventors showed that a regenerated tooth germ and regenerated tooth having a specific cell arrangement and directionality can similarly be obtained even by using oral epithelial cells and their first stage cultured cells as epithelial cells (for example, see Patent Literature 2), or by using amnion-derived cells as mesenchymal cells (for example, see Patent Literature 3), or else by using cells obtained by differentiation inducement of totipotent stem cells as mesenchymal cells (for example, see Patent Literature 4).

Also, in a regenerated tooth germ and regenerated tooth, the size of the tooth differs depending on its position and this size also varies with individuals. Therefore, it is important to control the size from the point of view of regenerating a tooth suitable to the position of the lost tooth. However, in the above documents, the control method for the size of regenerated teeth has not been examined. Furthermore, a set of regenerated teeth may be also obtained by the above method. In such a case, each tooth is separated from the set and used as a graft, but the difficulty in controlling the number of teeth and also the size of each tooth included in the set of teeth is easily expected from the point of view of insufficient development of the three-dimensional cell operation technology and insufficient understanding of the mechanism of form control in development biology.

The method for inoculating a cell mixture of a tooth germ including mesenchymal cells derived from the tooth pulp that form the dental bulb and dentin, and also including epithelial cells that contribute to the formation of the enamel in a scaffold made by solidification of a biodegradable polymer made from a copolymer of polyglycolic acid and polylactic acid, and then transplanting it into the body of an animal to form a tooth is also proposed as a method for producing regenerated teeth having the desired size and shape. In this method, the control of the shape of the tooth has been tested by using a scaffold of the desired shape. However, the regenerated tooth is derived from a tooth germ made from an epithelial cell layer and a mesenchymal cell layer, and the tooth germ is known to grow due to the chronological epithelical-mesenchymal interaction that occurs between the epithelial cells and mesenchymal cells. Thus, if a scaffold is used, sufficient cellular interaction is not obtained. Therefore, the use of a scaffold may not be preferable (for example, see Non-Patent Literature 1). Furthermore, the speed of formation of the tooth is faster than the time taken for the scaffold to decompose. Therefore, the tooth may be formed with some part of the scaffold mixed therein, and it is expected that the reproducibility of the cell arrangement and tooth shape may not necessarily be high.

On the other hand, it was believed that in general, the normal shape of the tooth crown cannot be obtained unless the mesenchymal tissue in the reconstructed tooth germ is perfect. However, it has been reported that even if a mesenchymal cell mass (mass obtained by centrifugal processing after separating the tissues with enzyme treatment) is used in place of mesenchymal tissue, when the number of cells is larger, a comparatively larger size of tooth germ is obtained in the in vitro culture, and the number of tooth cusps is also increased (for example, see Non Patent Literature 1). However, even after transplanting this tooth germ inside a living organism, the shape of the tooth crown and the number of tooth cusps change as compared to a normal tooth, and a tooth with the correct shape is not obtained. According to the report, a tooth with a correct shape is not obtained even by reconstructing through the combination of an epithelial cell mass and a mesenchymal cell mass. According to the report, in the reconstructing using an epithelial tissue and a mesenchymal cell mass, the correct shape can be created if mesenchymal tissue can be used, however, the limitation imposed during the producing of teeth regarding the use of unified mesenchymal cells indicates that partial resolution is achieved by increasing the number of cells.

Furthermore, it has been reported that when a reconstructed tooth germ is produced with an epithelial tissue and a mesenchymal cell mass, the number of produced teeth increases when the number of mesenchymal cells is increased, however, the size of the teeth is not affected (Non-Patent Literature 2). In the report, the final size of a tooth and tooth cusp is determined by intrinsic factors of the mesenchymal tissue and epithelial tissue, that is, it is concluded that the mesenchymal cells and epithelial cells have an intrinsic memory concerning the final size of a tooth and tooth cusp, respectively.

Furthermore, the present inventors figured out a method for using as many epithelial tissues in the region configuring the enamel knot as the desired number of teeth to form an epithelial cell aggregate, when producing a reconstructed tooth germ using an epithelial cell aggregate and a mesenchymal cell aggregate as a method for controlling the number and form of the teeth to be produced (Patent Literature 5). According to the method, an aggregate of teeth having a desired number of teeth can be obtained. However, as many epithelial tissues as the number of the desired teeth must be acquired to constitute the region configuring the enamel knot. Furthermore, Patent Literature 5 does not examine the control of the size of a tooth.

RELATED ART

Patent Literature

[Patent Literature 1]
WO 2006/129672
[Patent Literature 2]
Japanese Published Unexamined Patent Application No. 2008-29756
[Patent Literature 3]
Japanese Published Unexamined Patent Application No. 2008-206500
[Patent Literature 4]
Japanese Published Unexamined Patent Application No. 2008-200033
[Patent Literature 5]
Japanese Published Unexamined Patent Application No. 2008-29757

Non Patent Literature

[Non Patent Literature 1]
Hu et al. Tissue Engineering Volume 12, Number 8, 2006, 2069-2075
[Non Patent Literature 2]
J. Cai et al. Developmental Biology 304 (2007) 499-507

SUMMARY OF THE INVENTION

Problems to be Solved by the Invention

Teeth have a size and shape suitable to their function depending on the site at which they grow, and the size and shape are different depending on the site even for the same molar tooth. Furthermore, the size of a tooth varies from individual to individual. Therefore, when producing a regenerated tooth germ and a regenerated tooth as a treatment for lost teeth, it is very important to control its size such that it can function appropriately in the individual where the tooth is transplanted.

Furthermore, according to the experience of the inventors, the size of the regenerated tooth germ can change by various conditions, and because of the "memory" specific to the cells, teeth with good reproducibility and the same size are not obtained.

Therefore, an object of the present invention is to provide a method for producing a tooth having a desired size, in particular, a tooth of which the width of a tooth crown is a desired length.

Solving Means

As a result of intense studies to resolve the above problems, the present inventors found that the width of the crown of a regenerated tooth depends on the contact length in the predetermined direction of the mesenchymal cell aggregate and the epithelial cell aggregate in the support carrier, and does not depend on the number of each of these cells, and therefore, by adjusting this contact length, the width of the crown of the regenerated tooth can be controlled. Furthermore, it was found that when the mesenchymal cell aggregate and epithelial cell aggregate were respectively formed in an almost column shape, then by controlling a contact length of the axial direction of the column, a tooth having a desired length in one direction can be formed; particularly, by setting the contact length within the range between plus and minus 25% (±25%) of the desired length, a regenerated tooth having a desired length can be obtained; and along with the control of the size of the tooth, the number of tooth cusps can also be controlled; and by setting the contact length to below the predetermined numerical value, a single tooth could be obtained, and thereby the present invention was concluded.

That is, the present invention relates to:

[1] a method for producing a tooth having a desired length in one direction, comprising:

a step of arranging a first cell aggregate and a second cell aggregate in close contact inside a support carrier, wherein the first cell aggregate and the second cell aggregate are respectively composed of either one of mesenchymal cells and epithelial cells; and a step of culturing the first and second cell aggregates inside the support carrier, wherein the size of the tooth is adjusted by adjusting a contact length of the predetermined one direction of the first cell aggregate and the second cell aggregate;

[2] a method for producing a tooth having a desired length in one direction, comprising:

a step of producing a plurality of types of structures in which the first cell aggregate and the second cell aggregate are arranged in close contact inside a support carrier by changing the contact length of the predetermined one direction of the first cell aggregate and the second cell aggregate, wherein the first cell aggregate and the second cell aggregate are respectively composed of either one of mesenchymal cells and epithelial cells;

a step of culturing each of the plurality of types of structures inside the support carrier;

a step of measuring the length of one direction of the tooth produced in the preceding step and determining a correlation between the length and the contact length;

a step of calculating, based on the correlation, the contact length of the first cell aggregate and the second cell aggregate which is required for obtaining a tooth having a desired length in one direction;

a step of arranging the first cell aggregate and the second cell aggregate in close contact so as to have the contact length calculated in the preceding step, inside a support carrier, wherein the first cell aggregate and the second cell aggregate are respectively composed of either one of mesenchymal cells and epithelial cells; and a step of culturing the first and second cell aggregates inside the support carrier;

[3] a method for producing a tooth having a desired length in one direction, comprising:

a step of producing a plurality of types of structures in which an almost column-shaped first cell aggregate and second cell aggregate are arranged in close contact inside a support carrier such that the axial direction of each column is parallel, by changing a contact length of the axial direction of the first cell aggregate and the second cell aggregate, wherein the first cell aggregate and the second cell aggregate are respectively composed of either one of mesenchymal cells and epithelial cells;

a step of culturing each of the plurality of types of structures inside the support carrier;

a step of measuring the length of one direction of the tooth produced in the preceding step and determining a correlation between the length and the contact length;

a step of calculating, based on the correlation, the contact length of the first cell aggregate and the second cell aggregate which is required for obtaining a tooth having a desired length in one direction;

a step of arranging the almost column-shaped first cell aggregate and second cell aggregate in close contact inside the support carrier such that the contact length of the axial direction is the length calculated in the preceding step and the axial direction of each column is parallel, wherein the first cell aggregate and the second cell aggregate are respectively composed of either one of mesenchymal cells and epithelial cells; and a step of culturing the first and second cell aggregates inside the support carrier;

[4] A method for producing a molar tooth having a desired length in a mesiodistal direction and/or a buccolingual direction, comprising:

a step of producing a plurality of types of structures in which an almost column-shaped first cell aggregate and second cell aggregate are arranged in close contact inside a support carrier such that the axial direction of each column is parallel, by changing a contact length of the axial direction of the first cell aggregate and the second cell aggregate and/or a contact length of the direction perpendicular to the axis, wherein the first cell aggregate and the second cell aggregate are respectively composed of either one of mesenchymal cells and epithelial cells;

a step of culturing each of the plurality of types of structures inside the support carrier;

a step of measuring the length of the molar tooth produced in the preceding step in the mesiodistal direction and/or the buccolingual direction, and then determining a correlation between the contact length of the axial direction and the length of the mesiodistal direction of the molar tooth, and/or a correlation between the contact length perpendicular to the axis and the length of the buccolingual direction of the molar tooth;

a step of calculating, based on the correlation, the contact length of the axial direction of the first cell aggregate and the second cell aggregate and/or the contact of the direction length perpendicular to an axis which are required for obtaining the molar tooth having a desired length in a mesiodistal direction and/or a buccolingual direction;

a step of arranging the almost column-shaped first cell aggregate and second cell aggregate in close contact inside the support carrier such that the contact length of the axial direction and/or the contact length of the direction perpendicular to the axis is the length calculated by the preceding step and the axial direction of each column is parallel, wherein the first cell aggregate and the second cell aggregate are respectively composed of either one of mesenchymal cells and epithelial cells; and a step of culturing the first and second cell aggregates inside the support carrier;

[5] a method for producing a tooth having a desired length in one direction, comprising:

a step of arranging an almost column-shaped first cell aggregate and second cell aggregate in close contact inside a support carrier such that the axial direction of each column is parallel, whereby a contact length of the axial direction of the first cell aggregate and the second cell aggregate is approximately within the range between plus and minus 25% of the desired length, wherein the first cell aggregate and the second cell aggregate are respectively composed of either one of mesenchymal cells and epithelial cells; and a step of culturing the first and second cell aggregates inside the support carrier;

[6] the method according to the above [5], wherein the step of arranging the first and the second cell aggregates inside the support carrier comprises:

a step of producing a plurality of structures in which the first and the second cell aggregates are arranged inside the support carrier;

a step of measuring a contact length of an axial direction of the first and the second cell aggregates; and a step of selecting a structure of which the measured contact length is approximately within the range between plus and minus 25% of the desired length.

[7] a method for producing a single tooth, comprising:

a step of arranging a first cell aggregate and a second cell aggregate in close contact inside a support carrier, wherein the first cell aggregate and the second cell aggregate are respectively composed of either one of mesenchymal cells and epithelial cells; and a step of culturing the first and second cell aggregates inside the support carrier, wherein a maximum contact length of the first cell aggregate and the second cell aggregate is equal to or less than a predetermined value.

[8] the method according to any one of the above [1] to [7], wherein both the cell aggregates are cell masses;

[9] the method according to any one of the above [1] to [8], wherein at least one of the mesenchymal cell and the epithelial cell is derived from a tooth germ;

[10] a method for recovering a tooth missing part within an oral cavity, comprising:

a step of transplanting the tooth obtained by the method according to any one of the above [1] to [9], into the missing part;

[11] the method according to the above [10], wherein the tooth obtained by the method according to any one of the above [1] to [9] is transplanted as is into the missing part without dividing the tooth into two or more parts;

[12] the method according to the above [10] or [11], wherein the mesenchymal cell and the epithelial cell are derived from an individual having the missing part;

[13] the method according to any one of the above [10] to [12], wherein the oral cavity is an oral cavity of a non-mammal;

[14] A method for designing a method for producing a tooth having a desired length in one direction under a predetermined condition, wherein the designing method includes a method for determining, when the first cell aggregate and the second cell aggregate in close contact inside a support carrier and the first cell aggregate and the second cell aggregate are respectively composed of either one of mesenchymal cells and epithelial cells, a contact length of a predetermined one direction of the both cell aggregates, which is required for producing a tooth having a desired size, and wherein the method for determining the contact length further includes:

a step of producing a plurality of types of structures in which the first cell aggregate and the second cell aggregate are arranged in close contact inside a support carrier by changing the contact length of the predetermined one direction of the first cell aggregate and the second cell aggregate, wherein the first cell aggregate and the second cell aggregate are respectively composed of either one of mesenchymal cells and epithelial cells;

a step of culturing each of the plurality of types of structures inside the support carrier;

a step of measuring the length of one direction of the tooth produced in the preceding step, and then determining a correlation between the contact length and the length of one direction of the tooth; and a step of calculating, based on the correlation, the contact length of the first and second cell aggregates which is required for obtaining the tooth having a desired length in one direction.

[15] a method for designing a method for producing a single tooth under a predetermined condition, wherein the designing method includes a method for determining, when the first cell aggregate and the second cell aggregate are arranged in close contact inside a support carrier, a maximum contact length of the both cell aggregates and the first cell aggregate and the second cell aggregate are respectively composed of either one of mesenchymal cells and epithelial cells, which is required for producing a single tooth, and wherein the method for determining the maximum contact length further includes:

a step of producing a plurality of types of structures in which the first cell aggregate and the second cell aggregate are arranged in close contact inside a support carrier by changing the maximum contact length of the first cell aggregate and the second cell aggregate, wherein the first cell aggregate and the second cell aggregate are respectively composed of either one of mesenchymal cells and epithelial cells;

a step of culturing each of the plurality of types of structures inside the support carrier;

a step of measuring the number of teeth produced in the preceding step and determining the maximum contact length of the first cell aggregate and the second cell aggregate which is required for obtaining a single tooth; and

[16] the method according to the above [14] or [15], wherein at least one of the mesenchymal cell and the epithelial cell is derived from a tooth germ.

Effects of the Invention

According to the present invention, when the mesenchymal cell aggregate and the epithelial cell aggregate are arranged in close contact inside the support carrier, then by adjusting a contact length of the predetermined direction of the mesenchymal cells and epithelial cells, the width of the tooth crown in the contact length direction can be controlled in the regenerated tooth germ and regenerated tooth that are produced.

Particularly, when the mesenchymal cell aggregate and epithelial cell aggregate is formed in an almost column shape, then by controlling a contact length of the axial direction of the column, a tooth having a desired length in the axial direction can be formed.

Furthermore, it is also possible to design the method for producing a tooth including determining the contact length to enable the production of a tooth having the desired size based on the present invention.

Furthermore, according to the method for the present invention, regardless of the number of cells included in each cell mass, if the predetermined contact length can be obtained, a tooth having a desired length can be produced, and therefore, the desired size can be achieved effectively with a fewer number of cells.

Furthermore, in the present invention, by setting the contact length between each cell mass to below the predetermined value, a single tooth can be obtained instead of an aggregate of a plurality of teeth. Therefore, instead of passing through the step of segregation, the tooth can be used as is in the form of a graft.

DESCRIPTION OF EMBODIMENTS

Figure 1:
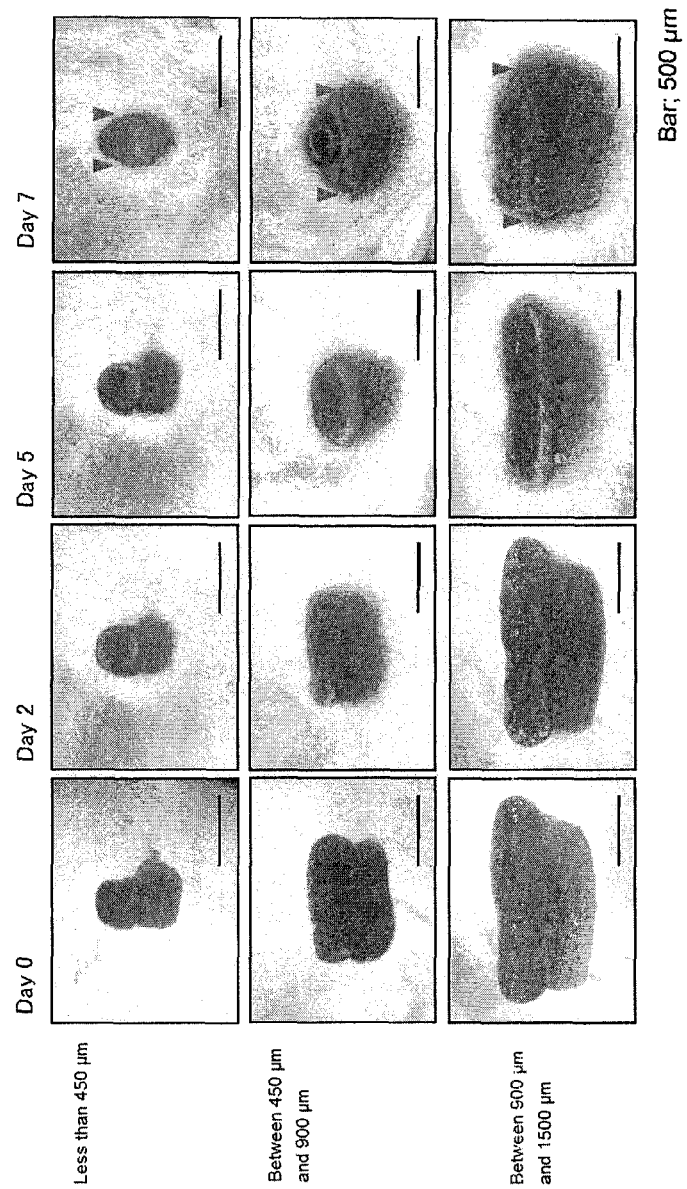
FIG. 1 shows the phase contrast microscopy of the organ culture on day zero, the second day, fifth day, and seventh day, when a contact length of the epithelial cell aggregate and mesenchymal cell aggregate during the producing of reconstructed tooth germ is set to less than 450 μm, between 450 μm and 900 μm, and between 900 μm and 1500 μm. The arrow heads in the figure show both ends of the tooth crown region that will form the future tooth crown.

A method for producing a desired tooth according to the present invention includes: a step of arranging a first cell aggregate and a second cell aggregate composed respectively of either one of mesenchymal cells and epithelial cells in close contact inside a support carrier; and a step of culturing the first and second cell aggregates inside the support carrier, wherein the size of the tooth is adjusted by adjusting a contact length of one direction of the first and second cell aggregates.

In the present invention, a "tooth" refers to a tissue comprising a layer of dentin on the inner side and a layer of enamel on the outer side in continuation, and having a directionality comprising the tooth crown and the dental root. The directionality of a tooth can be identified by the arrangement of the tooth crown and dental root. The tooth crown and dental root can be checked visually based on the shape and histological staining. The tooth crown is a part having a layered structure comprising enamel and dentin, and the dental root does not have the enamel layer.

Dentin and enamel may be easily and morphologically identified by those skilled in the art by histological staining or the like. Furthermore, the enamel can be identified by the presence of enamel blast cells, and the presence of enamel blast cells can be confirmed by the presence of amelogenin. On the other hand, the dentin can be identified by the presence of odontoblasts, and the presence of odontoblasts can be confirmed by the presence of dentin sialoprotein. The confirmation of amelogenin and dentin sialoprotein can be performed easily by methods well known in this field, for example, in situ hybridization and antibody staining can be used.

In the present invention, "tooth germ" and "tooth bud" are expressions used to specifically refer to different stages of generation of teeth. In this case, the tooth germ refers to the initial germ of a tooth that is determined to become a tooth in the future, and indicates from the bud stage to the bell stage that are generally used as the stages of generation of a tooth, and is a tissue in which the accumulation of dentin and enamel, which is characterized as hard tissues of a tooth, are not particularly identified. On the other hand, the "tooth bud" indicates a tissue after the stage of the "tooth germ" used in the present invention, and is a tissue that ranges from the stage when the dentin and enamel accumulation characterized as the hard tissues of the tooth have started to form, up to the stage before the tooth erupts from the gums and generally starts functioning as a tooth. The generation of a tooth from the tooth germ occurs through each of the bud stage, cap stage, and the early bell stage and late bell stage. In the bud stage, the epithelial cells infold into the mesenchymal cells to thicken, and in the cap stage, the epithelial cells are infolded to encompass the mesenchymal cells. When the early bell stage and late bell stage are reached, the epithelial cell part becomes the outer enamel, and the mesenchymal cell part forms the dentin on the inner side. The generation of the tooth germ is controlled by the cellular interaction between the epithelial cells and mesenchymal cells via cytokine, thereby forming a tooth.

In the present invention, "mesenchymal cells" refer to the cells derived from the mesenchymal tissue as well as the cells obtained by culturing such cells, and "epithelial cells" refer to cells derived from the epithelial tissue as well as the cells obtained by culturing such cells.

Furthermore, in the present invention, the "peridontal tissue" refers to the alveolar bone and the periodontal membrane formed mostly on the outer layer of the tooth. Those skilled in the art can easily identify the form of the alveolar bone and periodontal membrane through a histological staining.

In the present invention, the "step of arranging a first cell aggregate and a second cell aggregate composed respectively of either one of mesenchymal cells and epithelial cells in close contact inside a support carrier (hereinafter referred to as the "arrangement step") is, for example, described in Patent Literatures 1 to 5, and its entire disclosure is incorporated herein for the purpose of reference.

The above-mentioned first cell aggregate and the second cell aggregate are formed substantially from only mesenchymal cells or epithelial cells, respectively. "Formed substantially from only mesenchymal cells" implies that in the present invention, one of the aggregates of cells performs the same functions as when composed only of mesenchymal cells, and does not include cells other than mesenchymal cells, to the extent possible. The same applies to "formed substantially from only epithelial cells."

Here, cell aggregate refers to cells in close contact, and could even be a cell mass prepared from discrete cells even in the case of tissues. The use of a tissue has the advantage of easily enabling acquisition of teeth with the correct cell arrangement and shape, but the amount that can be obtained is limited. Because cultured cells can also be used as cell mass, they are comparatively easier to obtain and therefore, more preferable. According to the method for the present invention, a regenerated tooth with the correct cell arrangement and shape can be obtained even by using a cell mass.

The mesenchymal cells and epithelial cells configuring the cell aggregate can be derived from any tissue of a living organism as long as a regenerated tooth can be generated from the regenerated tooth germ formed by using these cells. Preferably, from the point of view of effectively forming a tooth having a specific structure and directionality by reproducing the cell arrangement inside the living organism, at least one of these cell aggregates must be derived from the tooth germ. It is more preferable that both the mesenchymal cells and epithelial cells be derived from the tooth germ. From the point of view of juvenility and homogeneity of the stage of differentiation of cells, the tooth germ is desired to be in the stage between the bud stage and the cap stage.

Examples of the mesenchymal cells derived from other than a tooth germ include cells derived from other mesenchymal tissues in a living organism. Preferably, these are bone marrow cells and mesenchymal cells not containing blood cells, more preferably, mesenchymal cells in the oral cavity, bone marrow cells inside the jawbone, mesenchymal cells derived from cranial neural crest cells, mesenchymal precursor cells which can differentiate into the mesenchymal cells, and stem cells thereof. As far as mesenchymal cells are concerned, an example of using amnion-derived cells is described in Patent Literature 3, and an example of using cells obtained by differentiation inducement of totipotent stem cells is described in Patent Literature 4 as mesenchymal cells, and its entire disclosure is incorporated herein for the purpose of reference.

The epithelial cells may also be those derived from other than a tooth germ, and examples thereof include cells derived from other epithelial tissues in a living organism. Preferable examples of the epithelial cells include epithelial cells of skin, mucosa and gingiva in the oral cavity, and more preferable examples of the epithelial cells include immature epithelial precursor cells which can generate differentiated, for example, keratinized or parakeratinized, epithelial cells such as skin and mucosa. Examples of such immature epithelial precursor cells include non-keratinized epithelial cells and stem cells thereof. An example of using oral epithelial cells and their first stage cultured cells as epithelial cells is described in Patent Literature 2, and its entire disclosure is incorporated herein for the purpose of reference.

A tooth germ and other tissues may be collected from the jawbone or the like of various animals such as dogs and cats besides primates such as humans and monkeys and ungulates such as pigs, cows and horses, which are mammals; and rodents such as mice, rats and rabbits, which are small mammals. For the collection of the tooth germ and the tissue, a condition generally used for collecting a tissue may be applied without modification, and the tooth germ and the tissue may be collected under sterile conditions and stored in an appropriate preservation solution. Examples of a human tooth germ include the tooth germ of a third molar, which is the so-called wisdom tooth, as well as a fetal tooth germ, and, from the point of view of utilization of autogenous tissues, usage of the tooth germ of a wisdom tooth is preferable. In the case of mice, the tooth germ of a mouse with a fetal age of 10 to 16 days may be used.

During the preparation of the mesenchymal cells and epithelial cells from the tooth germ, the tooth germ isolated from its surrounding tissue is first divided into a tooth germ mesenchymal tissue and a tooth germ epithelial tissue based on their shapes. To facilitate isolation, an enzyme may be used at this time. Examples of the enzyme include dispase, collagenase and trypsin.

The cell masses according to the present invention indicate a mass of cells derived from the mesenchymal tissue or epithelial tissue, and may be prepared by aggregating the cells obtained by dispersing the mesenchymal tissue or epithelial tissue, or by aggregating the cells obtained from the first stage or passage culture of the cells.

Enzymes, such as dispase, collagenase and trypsin may be used to disperse the cells. To obtain a sufficient number of cells, a medium generally used for animal cell culture, such as Dulbecco's Modified Eagle Medium (DMEM), may be used as the medium for the culture during the first stage or passage culture of the dispersed cells prior to the preparation of the cell mass. A serum for promotion of cell growth may be added, or, as an alternative to the serum, a cellular growth factor such as FGF, EGF or PDGF or a known serum component such as transferrin may be added. In cases where serum is added, its concentration may be changed appropriately depending on the culture state, and may usually be about 10%. For the cell culture, normal culture conditions, such as those for culture in an incubator at 37° C. under 5% $CO_2$, may be applied. An antibiotic such as streptomycin may be added as appropriate.

To aggregate cells, centrifugal processing is performed for the cell suspension. When the mesenchymal cell mass and epithelial cell mass are formed in close contact, they must be maintained respectively at a high density to ensure the cell interaction. A high density state means a density almost equivalent to the density at which a tissue is constructed, for example, the high density is in the range of $5 \times 10^7$ cells/ml to $1 \times 10^9$ cells/ml, preferably $1 \times 10^8$ cells/ml to $1 \times 10^9$ cells/ml, and most preferably $2 \times 10^8$ cells/ml to $8 \times 10^8$ cells/ml. The methods for preparing a cell mass having such a high cell density are not limited, for example, cells may be aggregated and precipitated by centrifugation. The centrifugal processing is particularly desired since this conveniently enables achievement of the high density without impairing the cell activity. Such centrifugation may be carried out at a revolution speed equivalent to a centrifugal force of $300 \times g$ to $1200 \times g$, and preferably $500 \times g$ to $1000 \times g$, for three minutes to ten minutes. Centrifugation at lower than $300 \times g$ may not be able to increase the cell density sufficiently, while centrifugation at higher than $1200 \times g$ may cause damage to the cells.

In cases where high density cell masses are prepared by centrifugation, the centrifugation is normally carried out after preparing a suspension of cells in a container such as a tube used for cell centrifugation, and the supernatant is removed to the greatest extent possible, leaving the cells as the precipitates. Here, the volume of components other than the cells of interest (for example, a culture medium or a buffer solution) is preferably not more than the volume of the cells, and most preferably, components other than the cells of interest are not contained. If such high density cell aggregates are in close contact with each other inside the support carrier according to the method described later, a closely-packed cell is obtained, and the cell interaction is effectively exerted.

The support carrier used in the present invention may be one in which cells may be cultured, and is preferably a mixture with the above-described medium. The material of the support carrier is not particularly limited, for example, collagen, agarose gel, carboxy methyl cellulose, gelatin, agar, hydrogel, Cellmatrix (trade name), Mebiol Gel (trade name), Matrigel (trade name), elastin, fibrin, laminin, extracellular matrix mixture, polyglycolic acid (PGA), polylactic acid (PLA), and lactic acid/glycolic acid copolymer (PLGA) may be used. These support carriers may have a hardness with which the cells can be virtually maintained at the locations where the cell aggregates were positioned in the support carrier, and examples of these support carriers include those in the forms of a gel, fiber and solid. Of these, materials having the appropriate hardness and retention, such as collagen, agarose gel, carboxymethyl cellulose, gelatin, agar, hydrogel, Cellmatrix, Mebiol Gel, Matrigel, extracellular matrix mixture, elastin, fibrin, and laminin are preferable. In this case, the hardness with which the cells can be virtually maintained at their locations may be hardness which is applicable to three-dimensional culture, that is, a hardness with which the position of the cells can be maintained while hypertrophy of the cells due to their growth is not inhibited, and such hardness can be easily determined by those skilled in the art.

Furthermore, the support carrier used in the present invention may have a retention whereby the cells can maintain their close contact of cell aggregate without being dispersed. The "close contact" indicates that the above-mentioned high density mesenchymal cell aggregate and epithelial cell aggregate maintain the same level of density even in the vicinity of the contact surface of the mesenchymal cells and epithelial cells. If the support carrier that can retain the close contact is collagen, for example, its usage at the final concentration of 2 mg/ml to 3 mg/ml, that is, at a jelly strength of 120 g to 250 g according to the method conforming to JIS-K6503-1996 (measured as the load required to push down by 4 mm with a 12.7-mm dia. plunger) provides an appropriate hardness.

Even in the case of other types of support carriers, if similar strength is obtained with the similar evaluation method, it can be used as the support carrier in the present invention. Furthermore, by combining together one or more types of support carriers, a support carrier with a hardness equivalent to the desired jelly strength may also be obtained.

The methods of arranging the first cell aggregate and second cell aggregate inside the support carrier are not particularly limited, but if the cell aggregates is a cell mass, for example, the precipitate obtained above by centrifugation may be fed inside the support carrier with a micro syringe, etc., and arranged. If the cell aggregate is a tissue, it can be arranged at any position inside the support carrier by using the tip of the syringe needle.

In the present invention, the methods of arranging the first cell aggregate and the second cell aggregate in the support carrier in close contact with each other is not particularly limited, for example, after arranging one of the cell aggregates in the support carrier, the other cell aggregate may be positioned such that it presses against the first cell aggregate, and thus both can be set in close contact with each other. More specifically, by appropriately changing the position of the tip of the above-mentioned syringe needle in the support carrier, one of the cell aggregates can be made to press against the other cell aggregate. When using an epithelial tissue or a mesenchymal tissue as the cell aggregate, the surface of the tissue that was in contact with the mesenchymal tissue or the epithelial tissue in the original tooth germ may be arranged such that it is in contact with the other cell aggregate.

Further, after the arrangement, it is also preferable to set up a step of solidification of the support carrier. This enables the cell to further aggregate thus resulting in a higher-density state. For example, when collagen gel is used, solidification can be achieved by leaving to stand at the culture temperature for several minutes to several tens of minutes. By this, components inside the cell aggregate other than the cells are reduced to the minimum possible extent, and a higher-density state is achieved.

In the present invention, the "step of culturing the first and the second cell aggregate inside the support carrier (hereinafter referred to as the "culturing step") is described in the Patent Literatures 1 to 5, and its entire disclosure is incorporated herein for the purpose of reference.

The culturing period varies depending on the number of cells positioned in the support carrier and the states of the cell masses, as well as on the conditions under which the culturing step is carried out, and the type of animal, and those skilled in the art can appropriately select the time period. In the case of transplantation inside the oral cavity, a minimum of one day culturing period, and more preferably, a period of three days or more is desired to enable a functional tooth to erupt.

By increasing the length of the culturing period, a great deal of progress can be made in the formation of a reconstructed tooth germ including the formation of accumulations of dentin and enamel, formation of the tooth crown, and formation of the dental root. To achieve the desired state, for example, culturing can be performed for 6 days or more, 30 days or more, 50 days or more, 100 days or more, or 300 days or more, and the medium and culture conditions can also be changed during culturing.

The culturing step inside the support carrier may be performed only by the support carrier which includes the first and the second cell aggregates, or the culture may be performed in the presence of other animal cells.

In cases where the culture is performed only by the support carrier, the culture can be performed under normal conditions used for culturing of animal cells. Here, a serum derived from mammals, and various cellular factors which are known to be effective in growth and differentiation of these cells may be added to the culture. Examples of such cellular factors include FGF and BMP.

From the point of view of gas exchange and nutrient supply for the cell aggregates, and also from the point of view of performing the entire steps in vitro without any contact or mixing of other animal cells, it is preferable to use organ culture for culturing inside the support carrier. In organ culture, generally, culturing is performed by floating a porous membrane on a medium suitable for growth of animal cells and placing a support carrier having the first and the second cell aggregates, on the membrane. The porous membrane used herein is preferably a membrane having many pores with a diameter of 0.3 to 5 μm, and specific examples thereof include Cell Culture Insert (trade name) and Isopore Filter (trade name).

On the other hand, performing the culture inside the support carrier in the presence of other animal cells enables the early formation of a tooth having a specific cell arrangement in response to the actions of various cytokines and the like from the animal cells. Such culture in the presence of other animal cells may be performed by culturing ex vivo using isolated cells or cultured cells, and furthermore, the support carrier having the first and the second cell aggregates may be transplanted into a living organism to carry out culture in vivo.

Such transplantation into and culture in vivo is especially preferable since a tooth and/or a periodontal tissue can be formed at an early stage. Preferable examples of animals which can be used as a living organism include mammals, preferably non-human mammals such as pigs and mice, and the animal is more preferably derived from the same species as that of the tooth germ tissue. In cases where culturing is performed by transplanting into an animal that is not of the same species as the tooth germ tissue, it is preferable to use an animal which was altered to be immunodeficient. In order to develop an organ or tissue of animal cells as normally as possible, examples of a site in a living organism suitable for such in vivo growth preferably include beneath the subrenal capsule, mesentery (omentum), and subcutaneous site.

The culturing period after transplantation varies depending on the size of the tooth at the time of the transplantation and the size of the tooth to be developed, and may be typically 3 to 400 days. For example, the time period of transplantation beneath the subrenal capsule is preferably 7 to 60 days, although it varies depending on the size of the tooth germ to be transplanted and the size of the tooth to be regenerated.

Ex vivo preculture may be performed prior to the transplantation into the living organism. The preculture strengthens the bonds between cells and the bond between the first and the second cell aggregates to make the cellular interaction stronger. As a result, the cellular interaction can be strengthened, and the total growth period can be shortened.

The preculturing period is not particularly limited. For example, a period of three days or more, preferably seven days or more, is preferable since a tooth bud can be developed from a tooth germ during this period and thus the culturing period after the transplantation can be shortened. For example, in the case of transplantation and culture beneath the subrenal capsule, and organ culture as the preculture, the time period of the organ culture is preferably 1 to 7 days.

A tooth generated according to the above-mentioned arrangement step and culturing step has a tooth-specific cell arrangement (structure) having dentin inside and enamel outside, and preferably has directionality, that is, has a tip (tooth crown) and a root of a tooth at the correct position, enabling it to sufficiently function as a tooth. Therefore, the generated tooth can be widely used as an alternative to a tooth. Furthermore, it may be used in research for elucidation of the generation process of a tooth.

Furthermore, by extending the culturing period, in addition to the tooth itself, a periodontal tissue such as the alveolar bone and periodontal membrane, which support and stabilize teeth on the jaw bone can be formed. As a result, the practicality of the tooth after the transplantation can be further improved. Furthermore, only the periodontal tissue can be isolated and used.

The present invention is characterized in that the length of one direction of the tooth thus obtained is adjusted by adjusting a contact length of the predetermined one direction of the first cell aggregate and the second cell aggregate in the above-mentioned arrangement step.

The contact length can be adjusted depending on the size, shape, and position of the cell aggregate to be arranged inside the support carrier. For example, when arranging the cell mass inside the support carrier with a micro syringe, the size, shape, and position of the cell aggregate can be changed appropriately by changing the diameter of the syringe needle and by moving the tip of the needle inside the support carrier while extruding the cell mass, and a contact length of any optional direction of the two cell aggregates can be adjusted. When using a mesenchymal tissue and epithelial tissue as the cell aggregate, the shape and size of the tissue can be adjusted before arranging it inside the support carrier, and by adjusting their arrangement position inside the support carrier, a contact length of the two cell aggregates can be adjusted.

Furthermore, by producing a plurality of types of structures in which the first and the second cell aggregates have been arranged in close contact with each other inside the support carrier, and then measuring a contact length of both cell aggregates and selecting the structure in which the measured contact length is the desired length, a reconstructed tooth germ having the desired contact length can be obtained, and such a step is also included in "adjusting the contact length" in the present invention. The measurement of the contact length can be done, for example, by observing through a phase contrast microscope.

Here, the length of one direction of the tooth refers to the width of the tooth crown in any direction, for example, the width in the buccolingual direction (direction perpendicular to the row of teeth), and the width in the mesiodistal direction (direction parallel to the row of teeth) are ideally adopted, but not limited thereto. The measurement of the width of the tooth crown can be done properly by those skilled in the art.

It is noted that when a regenerated tooth germ is formed by adjusting a contact length of the predetermined one direction of the first cell aggregate and the second cell aggregate, normally, the length of the same direction as the contact length is adjusted in the tooth crown of the generated tooth.

One of the aspects according to the present invention of the method for producing a tooth having a desired length in one direction includes: a step of producing a plurality of types of structures in which the first cell aggregate and the second cell aggregate are arranged in close contact inside a support carrier by changing a contact length of a predetermined one direction of the first cell aggregate and the second cell aggregate; a step of culturing each of the plurality of types of structures inside the support carrier; a step of measuring the length of one direction of the tooth produced in the preceding step so as to determine a correlation between the contact length and the length of one direction of the tooth; and a step of calculating, based on the correlation, a contact length of the first cell aggregate and the second cell aggregate required for obtaining a tooth having a desired length in one direction.

The step of producing a plurality of types of structures in which the first cell aggregate and the second cell aggregate are arranged in close contact inside a support carrier by changing a contact length of one direction of the first cell aggregate and the second cell aggregate, and then the step of culturing each of the plurality of types of structures inside the support carrier can be executed according to the above-mentioned explanation of the arrangement step, the culturing step, and the method for adjusting the contact length.

The correlation between the contact length and the length of one direction of the tooth can be found according to a well-known method or a method conforming to the same. For example, various graphs expressing the relationship between the contact length and the length of the tooth (width of the tooth crown) may be created, or a formula expressing the relationship between the contact length and the length of the tooth may be created. Furthermore, the distribution of the contact length providing the length of one tooth may be examined, and the range of contact length providing the size of a predetermined tooth may be determined.

The step of calculating a contact length of the first cell aggregate and the second cell aggregate required for obtaining a tooth having a desired length in one direction based on the acquired correlation can be executed by inserting the acquired size of the tooth in the above-mentioned formula and graph.

In this way, after determining the required contact length, a tooth with the desired size can be obtained by arranging the first cell aggregate and the second cell aggregate at the desired contact length in close contact with each other inside the support carrier under almost the same conditions as the above-mentioned arrangement step of the plurality of types of structures, and then performing a culture under almost the same conditions as the above-mentioned culturing conditions of the plurality of types of structures. Here, "almost the same conditions" refers to the conditions under which a tooth having the same length in one direction can be obtained with good reproducibility when the contact length is set to the same. In the arrangement step and culturing step for determining the contact length, and in the arrangement step and culturing step for producing a tooth having a desired length in one direction, it is desired, for example, that the culturing conditions, such as the type of the support carrier, temperature, constitution of the medium, and location of the culture (whether an organ culture or an in vivo culture) be the same.

Furthermore, when arranging the first and the second cell aggregates inside the support carrier, it is desired that a contact length of the part expected to form the position that must have the predetermined length in the tooth to be generated in the future be the length calculated above. Those skilled in the art can appropriately determine which directions of the contact surface of the first and second cell aggregates will become which directions in the tooth to be generated in the future. For example, when producing a molar tooth in which the length A of the mesiodistal direction is longer than the length B of the buccolingual direction, the contact surface of the first and second cell aggregates must be generally rectangular, and the longer side must form the contact length that provides length A in the mesiodistal direction.

Another aspect of the method for producing a tooth having a desired length in one direction according to the present invention includes: a step of producing a plurality of types of structures in which the almost column-shaped first cell aggregate and the second cell aggregate composed respectively of either one of mesenchymal cells and epithelial cells are arranged in close contact inside a support carrier such that the axial direction of each column is parallel by changing a contact length of the axial direction of the first cell aggregate and the second cell aggregate; a step of culturing each of the plurality of types of structures inside the support carrier; a step of measuring the length of the one direction of the tooth produced in the preceding step so as to determine a correlation between the contact length and the length; and a step of calculating, based on this correlation, a contact length of the first cell aggregate and the second cell aggregate required for obtaining a tooth having a desired length in one direction.

The step of producing a plurality of types of structures with different contact lengths and then performing the culturing step can be executed according to the above-mentioned explanation of the arrangement step, culturing step, and the method for adjusting the contact length. As described above, the correlation between the contact length and the length of one direction of the tooth can be expressed with a formula or graph, and the range of the contact length providing the predetermined tooth length can also be determined. Following this, a contact length of the first and second cell aggregates required for obtaining a tooth having a desired length in one direction can be determined based on these correlations.

In the present invention, the "almost column shape" refers to an elongated shape extending in one direction, such as an almost cylindrical shape and an almost prismatic shape. If the cell aggregate is a tissue, the tissue may be formed in an almost column shape and then arranged inside the support carrier. Furthermore, if the cell aggregate is cell mass, for example, the tip of the needle of a micro syringe can be positioned inside the support carrier, and the cell mass can be arranged in an almost cylindrical shape inside the support carrier by extruding the cells while moving the tip of the needle.

In this way, after determining the required contact length, a tooth having a desired length in one direction can be obtained by arranging the almost column-shaped first cell aggregate and the second cell aggregate at the contact length in close contact with each other inside the support carrier under almost the same conditions as the above-mentioned arrangement step of the plurality of types of structures, and then performing a culture under almost the same conditions as the above-mentioned culturing conditions of the plurality of types of structures.

Another aspect of the method for producing a tooth according to the present invention is a method for producing a molar tooth having a desired length in a mesiodistal direction and/or a buccolingual direction, and includes: a step of producing a plurality of types of structures in which the almost column-shaped first cell aggregate and the second cell aggregate composed respectively of either one of mesenchymal cells and epithelial cells are arranged in close contact inside a support carrier such that the axial direction of each column is parallel by changing a contact length of the axial direction and/or a contact length of the direction perpendicular to the axis of the first cell aggregate and the second cell aggregate; a step of culturing each of the plurality of types of structures inside the support carrier; and a step of measuring the length of the molar tooth produced in the preceding step in the mesiodistal direction and/or the buccolingual direction so as to determine a correlation between a contact length of the axial direction and the length of the mesiodistal direction of the molar tooth, and/or a correlation between a contact length perpendicular to the axis and the length of the buccolingual direction of the molar tooth.

As described above, generally, because the width of the buccolingual direction of a molar tooth is longer than the width of the mesiodistal direction, when the cell aggregate is formed in a column shape, the width of the tooth crown in the mesiodistal direction can be controlled by controlling the contact length in the axial direction, and the width of the tooth crown in the buccolingual direction can be controlled by controlling the contact length perpendicular to the axis.

A contact length of the axial direction and a contact length perpendicular to the axis may be changed with any method, for example, the length of the column-shaped cell aggregate, the diameter, and the distance between the axes of both cell aggregates may be changed. If the cell aggregate is a tissue, then by forming it into the desired diameter and length before arranging inside the support carrier, and then adjusting its position inside the support carrier, the contact length in the axial direction and the contact length perpendicular to the axis can be changed. Furthermore, if the cell aggregate is a cell mass, for example, when positioning it inside the support carrier with the help of a micro syringe, the diameter of the cell aggregate can be changed by changing the diameter of the needle, and by changing the distance in which the tip of the needle is moved inside the support carrier, the length of the axial direction of the cell aggregate can be changed. Furthermore, after arranging one cell aggregate, by adjusting the position in which another cell aggregate is arranged, the distance between the axes of both cell aggregates can be changed. By reducing the distance between both axes such that they are pressing against each other, the contact surface of the cell aggregate becomes generally larger, and in this way, a contact length of the axial direction and a contact length of the direction perpendicular to the axis can be changed.

Besides these, the arrangement step, culturing step, and the steps of determining the correlation between the various lengths can be performed according to the earlier-mentioned methods.

In this way, after determining a contact length of the axial direction and/or a contact length of the direction perpendicular to the axis, a molar tooth having a desired length in a mesiodistal direction and/or a buccolingual direction can be obtained by arranging the almost column-shaped first cell aggregate and the second cell aggregate at the contact length in close contact with each other inside the support carrier under almost the same conditions as the above-mentioned arrangement step of the plurality of types of structures, and then performing a culture under almost the same conditions as the above-mentioned culturing conditions of the plurality of types of structures.

Furthermore, another aspect of the method for producing a tooth having a desired length in one direction according to the present invention includes a step of arranging the first and the second cell aggregates in close contact in an almost column shape in the arrangement step such that the axial direction of each column is parallel, and a contact length of the axial direction of the first and second cell aggregates is within the range between plus and minus 25%, preferably ±10% of the above-mentioned desired length.

As described later, the present inventors found that when an almost cylindrical shaped mesenchymal cell mass and epithelial cell mass are arranged in close contact inside a support carrier such that the axial direction of the circular column is parallel, the length of the tooth thus produced depends on a contact length of the axial direction of the circular column. Furthermore, it was found that by setting the contact length to approximately within the range between plus and minus 25%, preferably to approximately ±10% of the desired length, a tooth in which the width of the tooth crown of the mesiodistal direction is of the desired length could be obtained. Therefore, for example, if a tooth in which the width of the tooth crown of the mesiodistal direction is approximately X μm is to be produced, the first cell aggregate and the second cell aggregate may be formed in an almost column shape, and a contact length of the axial direction may be set between 0.75X μm and 1.25X μm, preferably between 0.9X μm and 1.1X μm.

The method for controlling a contact length of the almost column-shaped first and second cell aggregates can be performed according to the already explained method.

Furthermore, instead of preparing a cell aggregate having the desired length in the axial direction, a plurality of types of structures in which the almost column-shaped first cell aggregate and the second cell aggregate are arranged in close contact inside a support carrier may be produced, a contact length of the axial direction of both cell aggregates may be measured, the structure in which the measured contact length is the desired length may be selected, and the structure may be passed through the culturing step. The measurement of the contact length can be done, for example, by observing through a phase contrast microscope.

A method for producing a single tooth according to the present invention includes: a step of arranging a first cell aggregate and a second cell aggregate composed respectively of either one of mesenchymal cells and epithelial cells in close contact inside a support carrier; and a step of culturing the first and second cell aggregates inside the support carrier, wherein the maximum contact length of the first cell aggregate and the second cell aggregate is equal to or less than the predetermined value.

When an unexpected tooth aggregate was obtained according to the method for Patent Literature 1, the present inventors figured out that by controlling a contact length of the first and second cell aggregates, and by controlling the size of a tooth, a single tooth with good reproducibility can be obtained. This is probably because the first enamel knot that stipulates the number of teeth formed from the tooth germ is not formed in a number more than one within the predetermined distance. If a single tooth can be produced, there is no need to perform isolation before transplanting the acquired tooth.

It is noted that in the method for producing a single tooth according to the present invention, the "maximum contact length" refers to the length of the longest straight line from among the straight lines included in the contact surface of the first cell aggregate and the second cell aggregate.

Furthermore, if the method for producing a single tooth according to the present invention is applied to a mouse, a contact length of the first and second cell aggregates is preferably equal to or less than 3000 μm, and more preferably equal to or less than 1500 μm. It is noted that the contact length is preferably equal to or more than 100 μm, and more preferably equal to or more than 200 μm. The contact length can be controlled according to the already mentioned description.

In the present invention, a single tooth refers to the structure f tooth that can be transplanted into a living organism, which is characterized by the presence of a tooth crown, dental root, dental pulp, and dentin formed in continuity, with a periodontal bone and an alveolar bone formed around each tooth. Those skilled in the art can easily find the number of produced teeth.

A method for recovering a tooth missing part within an oral cavity according to the present invention includes a step of transplanting a tooth produced by the method for producing the tooth, according to the present invention into the tooth missing part. According to this method, a tooth matching the size of the missing part can be produced and transplanted.

In the method for recovering a tooth missing part within an oral cavity according to the present invention, it is possible to transplant a tooth germ or a tooth in any stage that is produced in the producing method according to the present invention. If the formation of the tooth crown can be seen, it is preferable to place the tooth crown on the inner side of the oral cavity. If the formation of the tooth crown cannot be seen, it is preferable to arrange the epithelial cell layer of the corresponding part of the tooth crown or the epithelial cell layer of the reconstructed tooth germ towards the inner side of the oral cavity. Furthermore, it is preferable to arrange the open part of the epithelial-mesenchymal cell layer of the reconstructed tooth germ on the opposite side of the inner side of the oral cavity. In this way, the tip of the tooth (the tooth crown) is towards the inner side of the oral cavity and has the same directionality as the surrounding teeth.

The missing part implies a part arranged in the gums due to the loss of teeth, and its shape is not particularly limited. As long as the regenerated tooth germ or tooth can be embedded, there are no particular limitations concerning the missing part and the type of the desired tooth.

The missing part is usually located at the jaw bone or the alveolar bone inside the oral cavity. Furthermore, along with the tooth loss, if the alveolar bone mass has also deteriorated, a well-known clinical method for regeneration of the bone to facilitate embedding of the implant, such as the GTR method (Guided Tissue Regeneration) may be used for the missing part to increase the bone mass. After positioning the tooth germ or the tooth in the cavity, it is preferable to stitch the site according to the normal process.

In the method for recovering a tooth missing part within the oral cavity according to the present invention, the animal on which the transplant is to be performed must preferably be of the same species as that from which the tooth germ used for producing of tooth is extracted, and more preferably must be the same individual as that from which the tooth germ is extracted. Mammals, such as human beings, cows, horses, pigs, dogs, cats, and mice can be used as the animal. Non-mammals may also be used.

Furthermore, the present invention also provides a method for designing a method for producing a tooth having a desired length in one direction under a predetermined condition. "Predetermined conditions" imply conditions where the support carrier, medium, and the culturing method have been identified. By executing under the predetermined condition, the producing method designed according to the method for designing a method for producing a tooth having a desired length in one direction under a predetermined condition, a tooth having a desired length in one direction can be obtained.

The above-mentioned designing method according to the present invention includes a method for determining, when the first cell aggregate and the second cell aggregate composed respectively of either one of mesenchymal cells and epithelial cells are arranged in close contact inside a support carrier, a contact length of both cell aggregates, which is required for producing a tooth having the predetermined length in one direction.

Here, the method for determining the contact length includes: a step of producing a plurality of types of structures in which the first cell aggregate and the second cell aggregate composed respectively of either one of mesenchymal cells and epithelial cells are arranged in close contact inside a support carrier by changing a Contact length of the predetermined one direction of the first cell aggregate and the second cell aggregate; a step of culturing each of the plurality of types of structures inside the support carrier; a step of measuring the length of one direction of the tooth produced in the preceding step so as to determine a correlation between the contact length and the size of the tooth; and a step of calculating, based on the correlation, a contact length of the first cell aggregate and the second cell aggregate required for obtaining a tooth having a desired length in one direction.

Furthermore, the present invention also provides a method for designing the method for producing a single tooth under predetermined conditions.

The above-mentioned designing method according to the present invention includes a method for determining, when the first cell aggregate and the second cell aggregate composed respectively of either one of mesenchymal cells and epithelial cells are arranged in close contact inside a support carrier, the maximum contact length of both cell aggregates, which is required for producing a single tooth.

Furthermore, the method for determining the maximum contact length includes: a step of producing a plurality of types of structures in which the first cell aggregate and the second cell aggregate composed respectively of either one of mesenchymal cells and epithelial cells are arranged in close contact inside a support carrier by changing the maximum contact length of the first cell aggregate and the second cell aggregate; a step of culturing each of the plurality of types of structures inside the support carrier; and a step of measuring the number of teeth produced in the preceding step so as to determine the maximum contact length of the first cell aggregate and the second cell aggregate required for obtaining a single tooth.

It is noted that the terms used herein are used to explain a specific embodiment, and are not intended to limit the invention.

Moreover, the term "include" used herein is intended to mean the presence of a matter described (member, step, element, numeral, etc.) except for a case where a different understanding should be exercised in light of context, and does not exclude the presence of a matter other than the above-described matter (member, step, element, numeral, etc.).

Unless there is a different definition, the terms used herein (including technical terms and scientific terms) carry the same meaning as that widely understood by those skilled in the art to which the present invention belongs. The terms used herein should be interpreted to carry the meaning integral to that in the present specification and the related technical field, unless a different definition is explicitly provided, and thus, these should not be idealized nor interpreted in an excessive perfunctory meaning.

There is a case where an embodiment of the present invention is explained with reference to a schematic drawing, and when the schematic diagram is employed, an exaggerated explanation may be introduced for the purpose of an explicit explanation.

Terms of "first", "second", etc., are used to express various elements, and it is understood that these elements should not be limited by the terms. These terms are used merely to distinguish between one element and another element. For example, it is possible to describe a first element as a second element, and similarly, the second element as the first element, without departing from the scope of the present invention.

Even in the above-mentioned designing method, the mesenchymal cells and epithelial cells can be derived from any tissue of a living organism as long as a regenerated tooth can be prepared from the reconstructed tooth germ formed by using these cells. Preferably, at least one of these cells must be derived from the tooth germ, and more preferably, both these cells must be derived from the tooth germ.

Hereinafter, the present invention will be explained in detail with reference to examples. However, the present invention can be embodied in various modes, and the present invention should not be interpreted as being limited to the examples described herein.

EXAMPLES (1) Preparation of Tooth Germ Epithelial Cells and Tooth Germ Mesenchymal Cells The tooth germ was reconstructed to form a tooth. A mouse is used as the experimental model.

From an embryo (at the fetal age of 14.5 days) of C57BL/6N mouse (purchased from Japan SLC, Inc.), a mandibular molar tooth germ tissue was removed under the microscope by a conventional method. The mandibular molar tooth germ tissue was washed with $Ca^{2+}$, $Mg^{2+}$-free phosphate buffer (PBS(−)), and treated at room temperature for two minutes with the enzyme solution which is PBS(−) supplemented with U/ml (final concentration) Dispase (manufactured by BD, Massachusetts, USA). This was followed by washing with DMEM (manufactured by Sigma, St. Louis, Mo.) supplemented with 10% FBS (manufactured by Invitrogen, Carlsbad, Calif.) three times. Subsequently, a DNase I solution (manufactured by Takara, Shiga, Japan) was added to a final concentration of 70 U/ml to disperse the tooth germ tissue, and the tooth germ epithelial tissue and tooth germ mesenchymal tissue was surgically separated using a 25 G injection needle (manufactured by Terumo, Tokyo, Japan).

The tooth germ epithelial tissue was washed with PBS(−) three times, and treated at 37° C. for 30 minutes with the enzyme solution which is PBS(−) dissolved with 100 U/ml (final concentration) Collagenase I (manufactured by Worthington, Lakewood, N.J.), and this process was repeated twice. The cells whose precipitate was recovered through centrifugation were treated at 37° C. for ten minutes with the enzyme solution which is PBS(−) dissolved with 0.25% Trypsin (final concentration) (manufactured by Signma). This was followed by washing cells with DMEM (manufactured by Sigma) supplemented with 10% FBS (manufactured by Invitrogen) three times. Subsequently, a DNase I solution (manufactured by Takara) was added to a final concentration of 70 U/ml to the cells, and a suspension of the tooth germ epithelial cells separated with pipeting was obtained.

On the other hand, the tooth germ mesenchymal tissue was washed with PBS(−) three times, and treated at 37° C. for 20 minutes with the enzyme solution which is PBS(−) dissolved with 100 U/ml (final concentration) Collagenase I (manufactured by Worthington). This was further treated for ten minutes with PBS(−) supplemented with 0.25% Trypsin (manufactured by Signma) and 100 U/ml Collagenase I (manufactured by Worthington). Subsequently, 70 U/ml DNase I solution (manufactured by Takara) was added to obtain a suspension of the tooth germ mesenchymal cells separated with pipeting.

(2) Preparation of Reconstructed Tooth Germ

Next, a reconstruction of tooth germ was carried out using the above-prepared tooth germ epithelial cells and tooth germ mesenchymal cells. In a 1.5 ml micro tube (manufactured by Eppendorf, Hamburg, Germany) to which silicone grease was applied, tooth germ epithelial cells or tooth germ mesenchymal cells suspended in DMEM (manufactured by Sigma) supplemented with 10% FBS (manufactured by Invitrogen) were added, and the cells were collected by centrifugation (for three minutes at 600×g) as precipitates. The supernatant of the culture medium after the centrifugation was removed as much as possible, and centrifugation was carried out again for three minutes at 600×g, followed by complete removal of the culture medium remaining around the precipitates of the cells under a stereoscopic microscope using GELoader Tip 0.5-20 μl (manufactured by Eppendorf).

To a petri dish to which silicone grease was applied, 30 μl of Celimatrix type I-A (manufactured by Nitta gelatin, Osaka, Japan) was added dropwise to prepare a collagen gel droplet as a support carrier. To this solution, the precipitate obtained after centrifugation of the tooth germ mesenchymal cells was placed quantitatively using a Hamilton syringe (7105KH PT-3, manufactured by HAMILTON, Reno, Nev.) to prepare a cell mass in the form of cylindrical shaped cell aggregate. Subsequently, tooth germ epithelial cells in the equal amount to the tooth germ mesenchymal cells were arranged in the same way to form a cell mass such that the respective sides of both cell masses are in contact with each other and the axial direction is parallel to the cylindrical shaped cell mass of the tooth germ mesenchymal cells prepared earlier, and a reconstructed tooth germ was prepared.

After this, the collagen gel drop was solidified by allowing it to stand for 20 minutes at 37° C., and the bond between the two cell masses was made strong. A culture vessel was prepared such that DMEM (manufactured by Sigma) supplemented with 10% FBS (manufactured by Invitrogen) is in contact with Cell Culture Inserts (PET membrane having a pore size of 0.4 μm; manufactured by BD). The solidified reconstructed tooth germ was transferred onto the membrane of Cell Culture Inserts in the culture vessel, to carry out organ culture on the Cell Culture Insert with the conventional method at 37° C., 95% RH, and 5% $CO_2$.

(3) Analyzing the Size of the Regenerated Tooth Germ with Organ Culture

The cylindrical-shaped cell aggregates of the epithelial cells and mesenchymal cells were arranged in contact with each other at a length less than 450 μm, between 450 μm and 900 μm, and between 900 μm and 1500 μm to form three groups of reconstructed tooth germs, and a reconstructed tooth germ was formed through organ culture (FIG. 1). The contact length between both the cell masses was measured with a phase contrast microscope.

Figure 2:
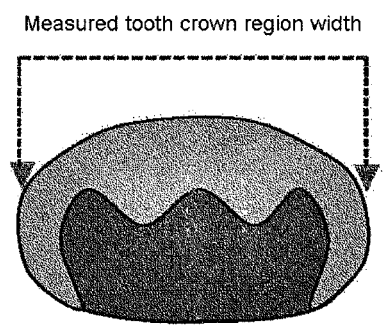
FIG. 2 is a schematic diagram showing the width of the tooth crown region that will form the future tooth crown, which is measured in the form of indexes showing the size of the regenerated tooth germ on the seventh day of the organ culture.

To analyze the width of the tooth crown region of the regenerated tooth germ, the width of the tooth crown region that would be the future tooth crown marked with the arrow heads in FIG. 2 was measured on the seventh day of organ culture in the regenerated tooth germ using a phase contrast microscope. The measurement position is also shown with arrows in the photograph on the seventh day in FIG. 1.

Figure 3:
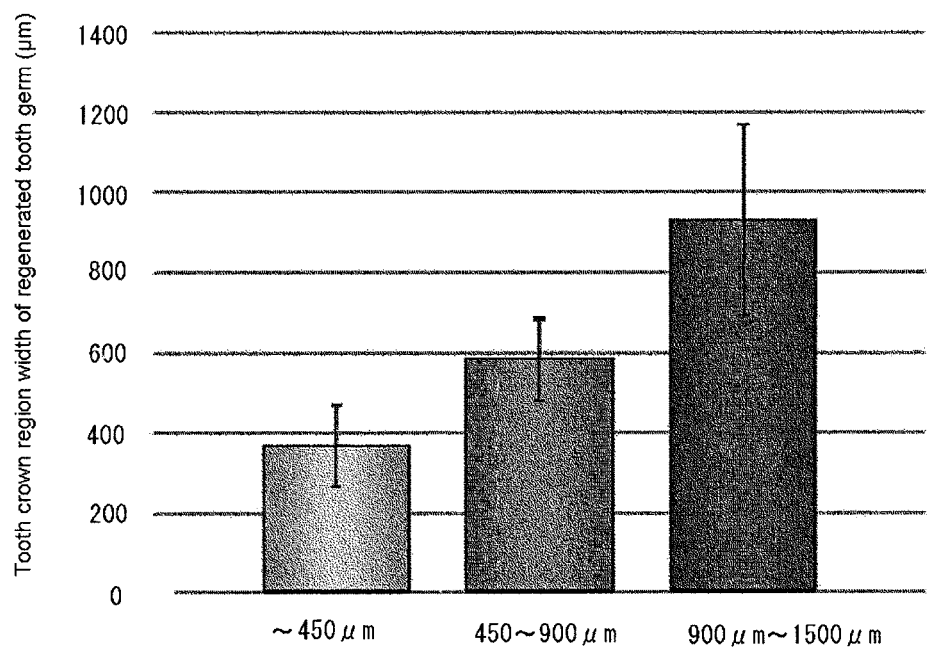
FIG. 3 is a bar graph showing the relationship between a contact length of the epithelial cell aggregate and mesenchymal cell aggregate during the producing of reconstructed tooth germ, and the size of the regenerated tooth germ on the seventh day of the organ culture.

The measurement results are shown in FIG. 3. For a contact length less than 450 μm, the width of the tooth crown region was 366±103.1 μm, for a contact length between 450 μm and 900 μm, the width of the tooth crown region was 584.0±103.3 μm, and for a contact length between 900 μm and 1500 μm, the width of the tooth crown region was 934.9±239.8 μm. This indicates that the longer the contact length of the epithelial cell aggregate and mesenchymal cell aggregate during the formation of the reconstructed tooth germ, the wider the tooth crown region on the regenerated tooth germ.

Figure 4:
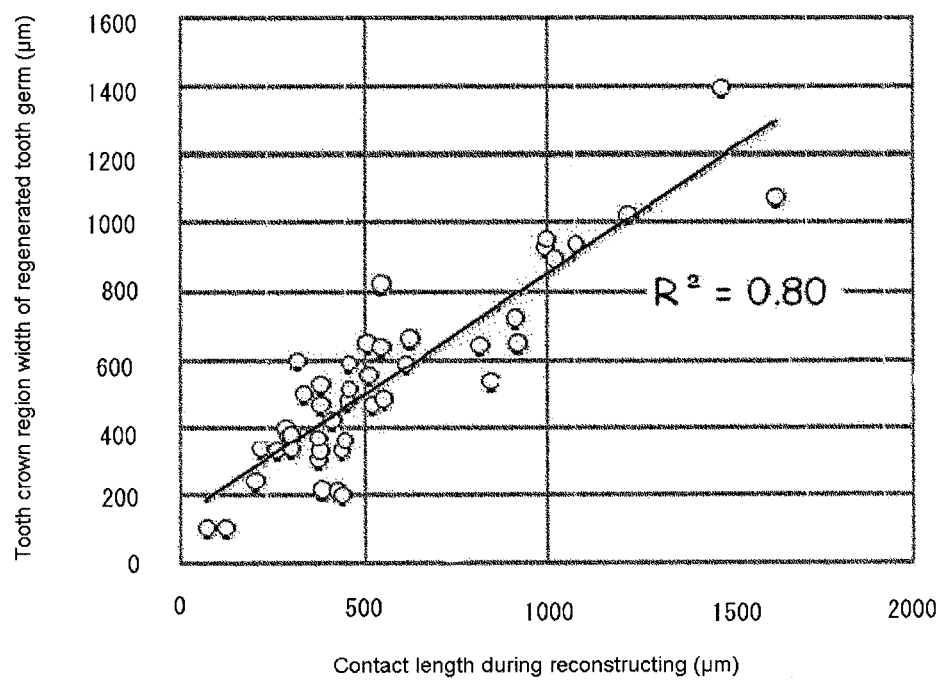
FIG. 4 is a graph showing the relationship between a contact length of the epithelial cell aggregate and mesenchymal cell aggregate during the producing of reconstructed tooth germ, and the size of the regenerated tooth germ on the seventh day of the organ culture.
Figure 5:
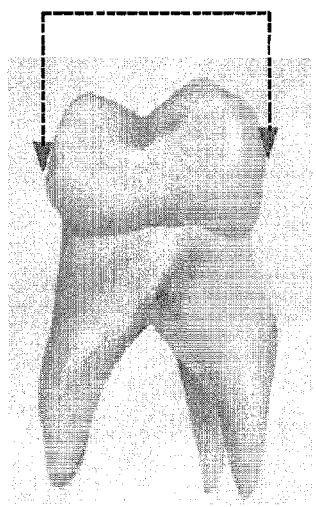
FIG. 5 is a schematic diagram showing the width of the tooth crown measured in the form of indexes showing the size of a regenerated tooth generated by transplanting a regenerated tooth germ beneath the subrenal capsule.

Furthermore, FIG. 4 is a scatter chart of the measured values of the contact length and the width of the crown region, and linear approximation is performed for the straight line in the figure with the least square method. The formula expressing the straight line was y=0.7114x+133.95.

(4) Analyzing the Size of the Regenerated Tooth by Subrenal Capsule Assay

From an eight-week old C57BL/6 mouse under anesthesia, the hair on the back located on top of the kidneys was shaved, the skin and the peritoneum were cut open to about 1 cm, and the kidneys were removed using ring tweezers (manufactured by Natsume, Tokyo, Japan). The subrenal capsule was cut open by 2 to 3 mm using a blade (manufactured by Feather, Tokyo, Japan). In the space between the kidneys and the subrenal capsule, the three groups of reconstructed tooth germs with different contact lengths as shown in example (2) were inserted with collagen gel, the kidneys were placed back, and the muscular coat and skin were stitched.

Figure 6:
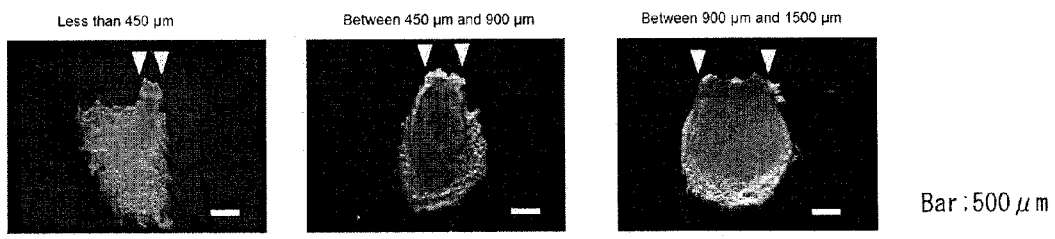
FIG. 6 shows a stereomicroscopic image of a regenerated tooth on the $21^{st}$ day of the subrenal capsule assay, when a contact length of the epithelial cell aggregate and mesenchymal cell aggregate during the producing of reconstructed tooth germ is set to less than 450 μm, between 450 μm and 900 μm, and between 900 μm and 1500 μm. The arrow heads in the figure show both ends of the tooth crown.

The regenerated tooth was extracted on the 21$^{st}$ day after subrenal capsule assay. The regenerated tooth that was extracted is shown in FIG. 6. The part marked with arrow heads in FIG. 6 was measured as the width of the tooth crown using a stereoscopic microscope.

The measurement results are shown in Table 1.

TABLE 1

| A<br>Contact length in reconstructed tooth germ (μm) | B<br>Actually-measured value of crown width of regenerated tooth (μm) | C<br>Difference in tooth crown size; (B − A) (μm) | D<br>Difference percentage; \|B − A\|/A × 100 (%) |
|---|---|---|---|
| 437.91 | 482.29 | 44.38 | 10.13 |
| 410.77 | 529.76 | 118.99 | 28.97 |
| 318.38 | 317.34 | (1.04) | 0.33 |
| 336.77 | 386.35 | 49.58 | 14.72 |
| 460.00 | 491.92 | 31.92 | 6.94 |
| 619.87 | 762.57 | 142.70 | 23.02 |
| 549.87 | 578.28 | 28.41 | 5.17 |
| 295.25 | 387.88 | 92.63 | 31.37 |
| 446.70 | 459.61 | 12.91 | 2.89 |
| 458.72 | 490.37 | 31.65 | 6.90 |
| 511.48 | 402.97 | (108.51) | 21.22 |
| 384.75 | 502.64 | 117.89 | 30.64 |
| 426.23 | 468.40 | 42.17 | 9.89 |
| 924.66 | 1017.47 | 92.81 | 10.04 |
| 1020.24 | 1240.64 | 220.40 | 21.60 |
| 996.84 | 979.63 | (17.21) | 1.73 |
| 1000.00 | 1083.81 | 83.81 | 8.38 |
| 1223.27 | 1293.17 | 69.90 | 5.71 |
| 915.86 | 989.76 | 73.90 | 8.07 |

The average value of the percentage expressed by D in the table was 13.03, and the standard deviation was 10.00.

Figure 7:
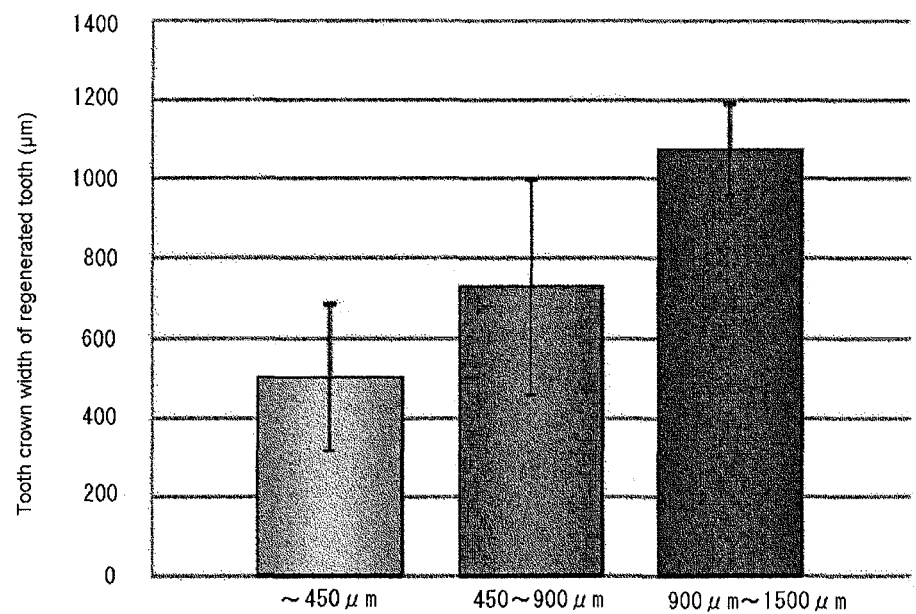
FIG. 7 is a bar graph showing the relationship between a contact length of the epithelial cell aggregate and mesenchymal cell aggregate during the producing of reconstructed tooth germ, and the width of the tooth crown of the regenerated tooth on the $21^{st}$ day of the subrenal capsule assay.

Furthermore, the width of the tooth crown obtained by dividing the above-mentioned measurement results into three based on a contact length of less than 450 μm, between 450 μm and 900 μm, and between 900 μm and 1500 μm is shown in FIG. 7. For a contact length less than 450 μm, the width of the tooth crown was 497±118.0 μm, for a contact length between 450 μm and 900 μm, the width of the tooth crown was 727.0±271.4 μm, and for a contact length between 900 μm and 1500 μm, the width of the tooth crown was 1073.9±186.0 μm. This indicates that the longer a contact length of the epithelial cell aggregate and mesenchymal cell aggregate during the formation of the reconstructed tooth germ, the wider the tooth crown on the regenerated tooth.

Figure 8:
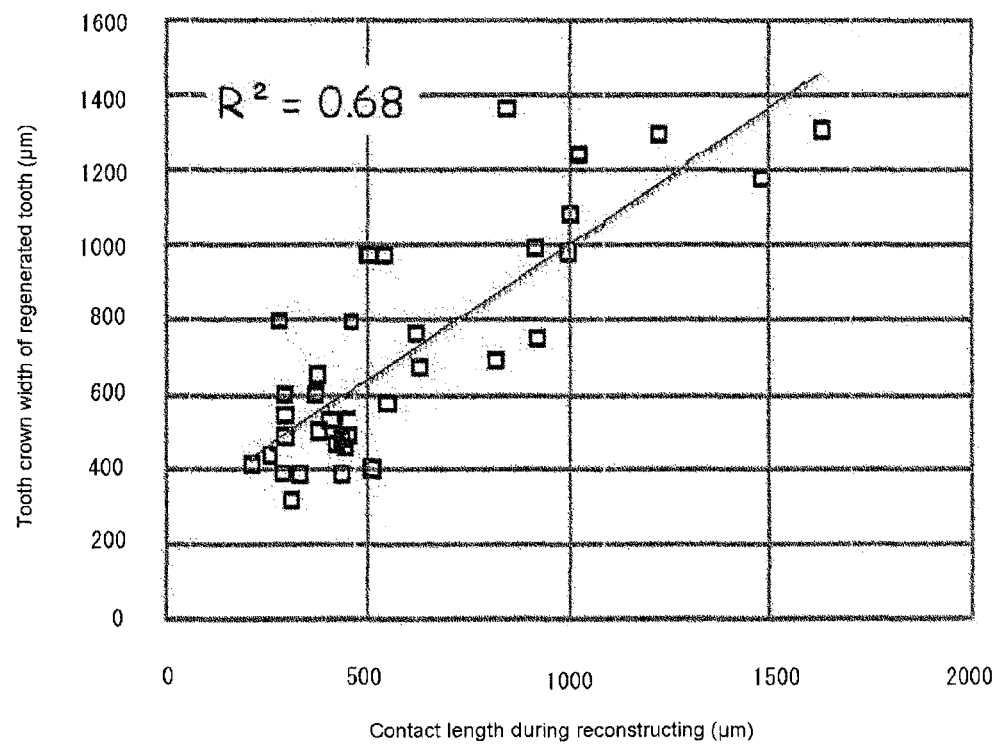
FIG. 8 is a graph showing the relationship between a contact length of the epithelial cell aggregate and mesenchymal cell aggregate during the producing of reconstructed tooth germ, and the width of the tooth crown of the regenerated tooth on the $21^{st}$ day of the subrenal capsule assay.

Furthermore, FIG. 8 is a scatter chart of the measured values of the contact length and the width of the tooth crown, and linear approximation is performed for the straight line in the figure with the least square method. The formula expressing the straight line was y=0.7257x+272.15.

(5) Analyzing the Number of Cusps of the Regenerated Tooth with a Micro CT

Figure 9:
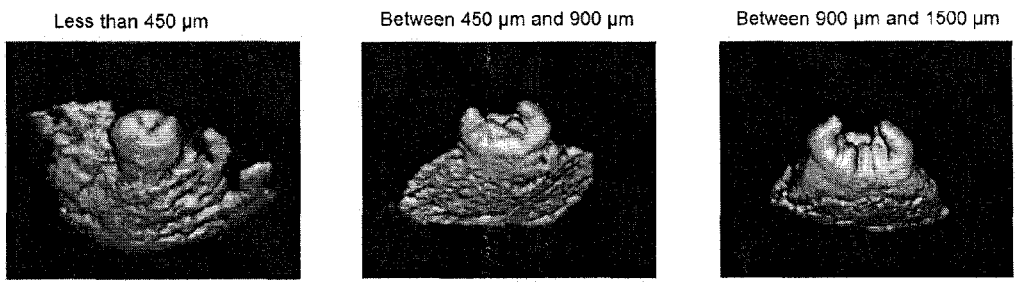
FIG. 9 is a CT image of a regenerated tooth on the $21^{st}$ day after the subrenal capsule assay, when a contact length of the epithelial cell aggregate and mesenchymal cell aggregate during the producing of reconstructed tooth germ is set to less than 450 μm, between 450 μm and 900 μm, and between 900 μm and 1500 μm.

Using a 3D micro X-ray CT for experimental animals (manufactured by RIGAKU, Tokyo, Japan), the regenerated tooth generated with the method shown in (4) was photographed at a voltage of 90.0 kv, electric current of 150.0 A with 10 μm/Pixel. The results are shown in FIG. 9.

Figure 10:
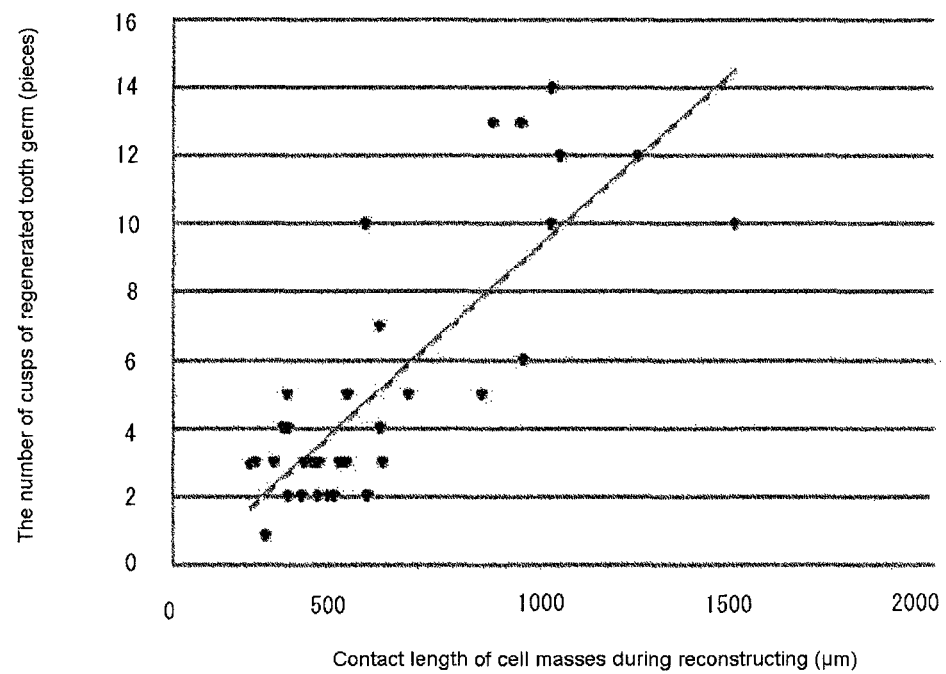
FIG. 10 is a graph showing the relationship between a contact length of the epithelial cell aggregate and mesenchymal cell aggregate during the producing of reconstructed tooth germ, and the number of cusps of the regenerated tooth after 21 days of the subrenal capsule assay.

Next, the image was analyzed using i-View (manufactured by RIGAKU, Tokyo, Japan), a 3D image of the regenerated tooth was taken, and the number of cusps of the regenerated tooth was counted. If a contact length of the cell masses of epithelial cells and mesenchymal cells during the producing of the reconstructed tooth germ, and the number of cusps of the regenerated tooth generated beneath the subrenal capsule are plotted and the correlation coefficient is calculated, a strong correlation is seen to exist between the contact length during reconstruction and the number of cusps of the regenerated tooth ($R^2$=0.658) (FIG. 10). This indicates that the longer a contact length of the epithelial cells and mesenchymal cells during reconstruction, the more the number of cusps in the regenerated tooth.

(6) Analyzing the Reconstructed Tooth Germ by Changing the Number of Cells with Contact Length of the Cell Aggregate within a Fixed Range A contact length of the cell masses was set in the range of 300 to 500 μm. By preparing a cell mass using a cell suspension of approximately 0.05 μl capacity with a Hamilton syringe having an internal diameter of 0.330 mm (7105KH PT-3, manufactured by HAMILTON, Reno, Nev.) as used in example (2), and by preparing a cell mass using a cell suspension of approximately 0.02 μl capacity with a Hamilton syringe having an internal diameter of 0.203 mm (7002KH PT-3, manufactured by HAMILTON), a reconstructed tooth germ in which the number of cells used for the cell masses was changed was prepared. The forms of the regenerated tooth germ and the regenerated tooth formed from this reconstructed tooth germ were analyzed by the methods shown in examples (3), (4), and (5).

Figure 11:
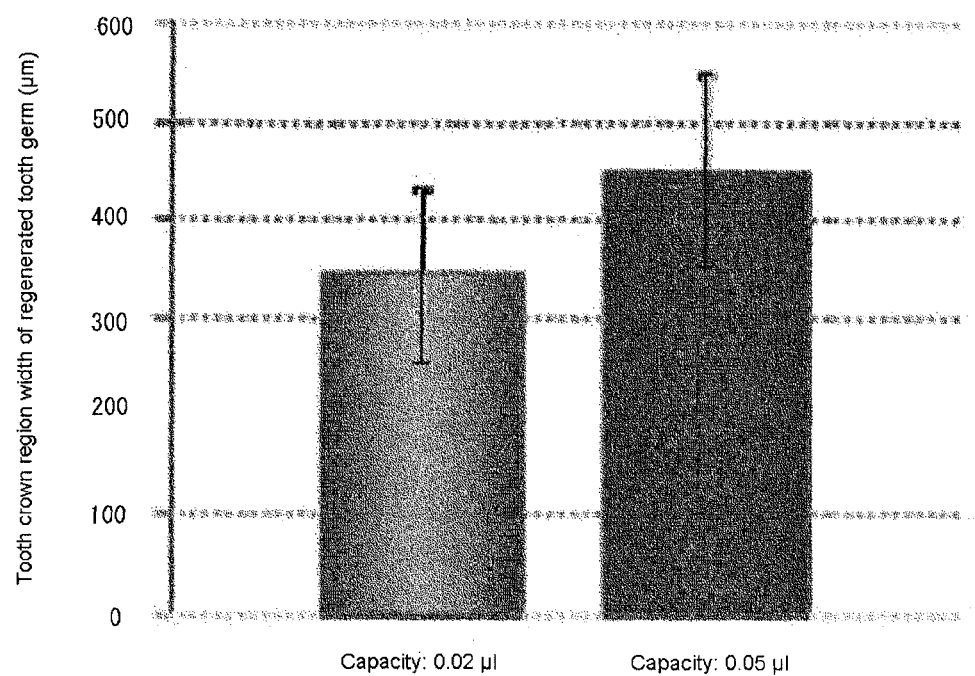
FIG. 11 shows the results of measurement of the width of tooth crown region of a regenerated tooth germ obtained when a contact length of the cylindrical epithelial cell aggregate and mesenchymal cell aggregate is set to a fixed range in the reconstructed tooth germ, and the number of cells included in each aggregate is changed.
Figure 12:
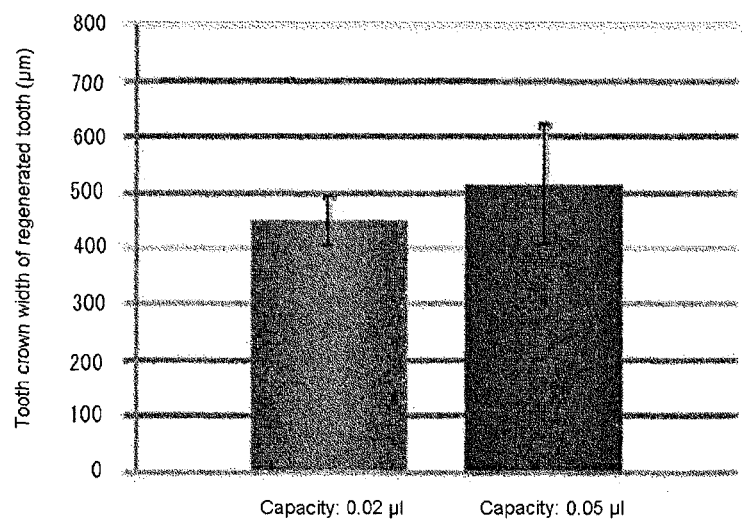
FIG. 12 shows the results of measurement of the width of tooth crown of a regenerated tooth obtained when a contact length of the cylindrical epithelial cell aggregate and mesenchymal cell aggregate is set to a fixed range in the reconstructed tooth germ, and the number of cells included in each aggregate is changed.
Figure 13:
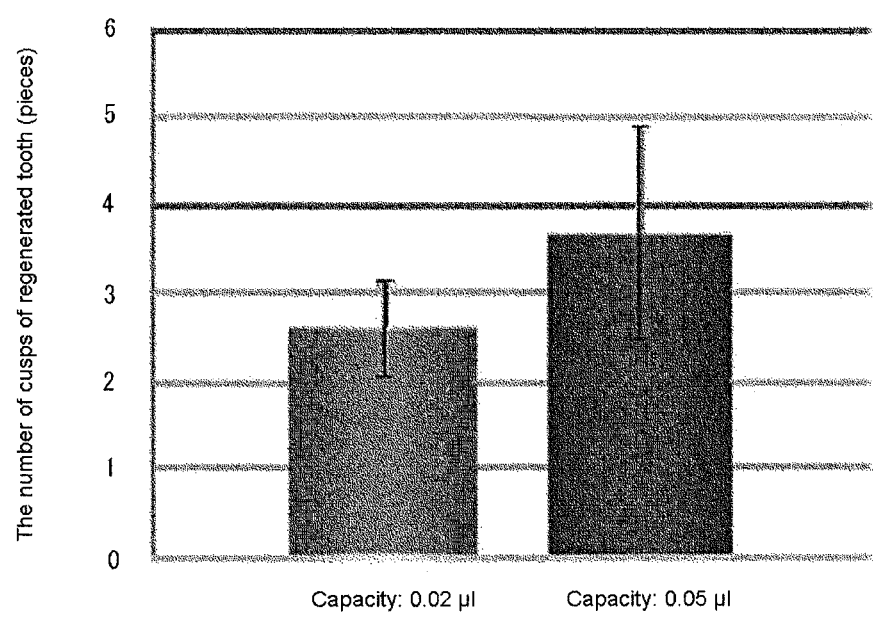
FIG. 13 shows the results of measurement of the number of cusps of a regenerated tooth obtained when a contact length of the cylindrical epithelial cell aggregate and mesenchymal cell aggregate is set to a fixed range in the reconstructed tooth germ, and the number of cells included in each aggregate is changed.

The width of the tooth crown region of the regenerated tooth germ is shown in FIG. 11, the width of the crown of the regenerated tooth is shown in FIG. 12, and the number of cusps in the regenerated tooth is shown in FIG. 13. Even if the number of cells is changed by keeping the contact length within a fixed range, no significant change was observed in the forms of the regenerated tooth germ and the regenerated tooth.

The invention claimed is:

1. A method for producing a tooth, comprising: a step of arranging, in a support carrier, a column-shaped first cell aggregate comprising mesenchymal cells to be in contact with a column-shaped second cell aggregate comprising epithelial cells, wherein at least one of the mesenchymal cell and the epithelial cell is derived from a tooth germ, wherein said first cell aggregate and said second cell aggregate are cell masses, wherein a contact length between said column-shaped first cell aggregate and said column-shaped second cell aggregate is approximately within a range of plus and minus 25% of a desired length, wherein the contact length is measured in a direction that parallels an axis of said first or second column-shaped cell aggregate; and a step of culturing said first and second column-shaped cell aggregates inside the support carrier, thereby producing a tooth.

2. A method for producing a tooth, comprising: a step of producing a plurality of structures, wherein each of the plurality of structures comprises a first cell aggregate and a second cell aggregate arranged in contact inside a first support carrier, wherein the plurality of structures are formed by changing contact lengths, in a selected direction, between said first cell aggregates and said second cell aggregates, wherein said first cell aggregate comprise mesenchymal cells and said second cell aggregate comprise epithelial cells, wherein at least one of the mesenchymal cell and the epithelial cell is derived from a tooth germ, wherein said first cell aggregate and said second cell aggregate are cell masses; a step of culturing each of the plurality of structures inside the first support carrier, such that teeth are produced; a step of measuring lengths, in the selected direction, of teeth produced from the plurality of structures in the preceding step and determining a correlation between the measured lengths and the contact lengths in each of the plurality of structures; and a step of calculating, based on the correlation, a contact length of a first cell aggregate and a second cell aggregate that is required for obtaining a tooth having a desired length in the selected direction; a step of arranging the first cell aggregate and the second cell aggregate, of the preceding step, in contact so as to have the contact length calculated in the preceding step, inside a second support carrier, wherein the first cell aggregate, of the preceding step, comprises mesenchymal cells and the second cell aggregate, of the preceding step, comprises epithelial cells; and a step of culturing the first and second cell aggregates, of the preceding step, inside the second support carrier, thereby producing a tooth.

3. A method for producing a tooth, comprising: a step of producing a plurality of structures, wherein each of the plurality of structures comprises a column-shaped first cell aggregate and a column-shaped second cell aggregate arranged in contact inside a first support carrier such that an axis of said column-shaped first cell aggregate parallels an axis of said column-shaped second cell aggregate, wherein the plurality of structures are produced by changing contact lengths, in an axial direction along the axis of said column-shaped first cell aggregate or along the axis of said column-shaped second cell aggregate, wherein said column-shaped first cell aggregates comprise mesenchymal cells and said column-shaped second cell aggregates comprise epithelial cells, wherein at least one of the mesenchymal cell and the epithelial cell is derived from a tooth germ, wherein the first cell aggregate and the second cell aggregate are cell masses; a step of culturing each of the plurality of structures inside the first support carrier, such that teeth are produced; a step of measuring a length in the axial direction for each tooth produced by the plurality of structures in the preceding step, and determining a correlation for the plurality of structures based on the measured length and the contact length in each of the plurality of structures; and a step of calculating, based on the correlation, a contact length between a column-shaped first cell aggregate and a column-shaped second cell aggregate that is required for obtaining a tooth having a desired length in the axial direction; a step of arranging the column-shaped first cell aggregate, of the preceding step, and the column-shaped second cell aggregate, of the preceding step, in contact inside a second support carrier such that the contact length in the axial direction is the length calculated in the preceding step; and a step of culturing the first and second cell aggregates, of the preceding step, inside the second support carrier, thereby producing a tooth.

4. A method for producing a molar tooth having a desired length in a mesiodistal direction and/or a buccolingual direction, comprising: a step of producing a plurality of structures, wherein each of the plurality of structures comprises a column-shaped first cell aggregate and a column-shaped second cell aggregate arranged in contact inside a first support carrier such that an axis of said column-shaped first cell aggregate parallels an axis of said column-shaped second cell aggregate, wherein the plurality of structures are produced by changing contact lengths between said column-shaped first cell aggregates and said column-shaped second cell aggregate, wherein the contact lengths are measured in an axial direction, which is parallel with said axis of said column-shaped first cell aggregate, and/or a perpendicular direction, which is perpendicular with said axis of said column-shaped first cell aggregate, wherein said column-shaped first cell aggregate comprise mesenchymal cells and said column-shaped second cell aggregate comprise epithelial cells, wherein at least one of the mesenchymal cell and the epithelial cell is derived from a tooth germ, wherein said first cell aggregate and said second cell aggregate are cell masses; a step of culturing each of the plurality of structures inside the first support carrier, such that molar teeth are produced; a step of measuring a length for each molar tooth produced in the preceding step in the mesiodistal direction, which is aligned with the axial direction, and/or the buccolingual direction, which is aligned with the perpendicular direction, and determining a correlation for the plurality of structures based on the contact length in each of the plurality of structures and the measured length for the molar tooth produced; a step of calculating, based on the correlation, a contact length between a first cell aggregate and a second cell aggregate that is required for obtaining a molar tooth having a desired length in a mesiodistal direction and/or a buccolingual direction; a step of arranging the column-shaped first cell aggregate, of the preceding step, and the column-shaped second cell aggregate, of the preceding step, in contact inside a second support carrier such that the contact length in the axial direction and/or the perpendicular direction is the length calculated in the preceding step; and a step of culturing the column-shaped first and second cell aggregates, of the preceding step, inside the second support carrier, thereby producing a molar tooth.

5. A method for producing a tooth having a desired length in one direction, comprising: a step of arranging a column-shaped first cell aggregate and a column-shaped second cell aggregate in contact inside a support carrier such that an axial direction of said column-shaped first cell aggregate parallels an axial direction of said column-shaped second cell aggregate and that a contact length in the axial direction of said first and second column-shaped cell aggregates is approximately within a range between plus and minus 25% of the desired length, wherein said column-shaped first cell aggregate comprise mesenchymal cells and said column-shaped second cell aggregate comprise epithelial cells, wherein at least one of the mesenchymal cell and the epithelial cell is derived from a tooth germ, wherein said first cell aggregate and the second cell aggregate are cell masses; and a step of culturing said first and second column-shaped cell aggregates inside the support carrier, such that a tooth having a desired length in one direction is produced.

6. A method for producing a single tooth, comprising: a step of arranging a column-shaped first cell aggregate and a column-shaped second cell aggregate in contact inside a support carrier; and a step of culturing said column-shaped first and said column-shaped second cell aggregates inside the support carrier, wherein said column-shaped first cell aggregate comprise mesenchymal cells and said column-shaped second cell aggregate comprise epithelial cells, wherein at least one of the mesenchymal cell and the epithelial cell is derived from a tooth germ, wherein said first cell aggregate and said second cell aggregate are cell masses; wherein a contact length between said column-shaped first cell aggregate and said column-shaped second cell aggregate is approximately within a range of plus and minus 25% of a desired length.

7. The method according to claim 1, wherein both the mesenchymal cell and the epithelial cell are derived from a tooth germ.

8. A method for restoring a missing tooth within an oral cavity, comprising:
a step of transplanting the tooth obtained by the method according to claim 1, into the oral cavity.

9. The method according to claim 8, wherein the tooth obtained by the method according to claim 1 is transplanted as is into the oral cavity without dividing the tooth into two or more parts.

10. The method according to claim 8, wherein the mesenchymal cell and the epithelial cell are derived from an individual having the missing tooth.

11. The method according to claim 8, wherein the oral cavity is an oral cavity of a non-mammal.

12. A method for determining a contact length needed to produce a tooth having a desired size, comprising a step of producing a plurality of structures, wherein each of the plurality of structures comprises a column-shaped first cell aggregate and an a column-shaped second cell aggregate arranged in contact inside a support carrier, wherein the plurality of structures are produced by changing contact lengths between said column-shaped first cell aggregate and said column-shaped second cell aggregate, wherein said first cell aggregate comprise mesenchymal cells and said second cell aggregate comprise epithelial cells, wherein at least one of the mesenchymal cell and the epithelial cell is derived from a tooth germ, wherein said first cell aggregate and said second cell aggregate are cell masses; a step of culturing each of the plurality of structures inside the support carrier, such that teeth are produced; a step of measuring a length in a selected direction of each tooth produced in the preceding step and determining a correlation for the plurality of structures based on the contact length in each of the plurality of structures and the measured length for the tooth produced by the plurality of structures in the preceding step; and a step of calculating, based on the correlation, the contact length between a first and a second column-shaped cell aggregate required for producing the tooth having the desired size.

13. A method for determining a maximum contact length required for producing a single tooth, comprising a step of producing a plurality of structures, wherein each of the plurality of structures comprises a first cell aggregate and a second cell aggregate arranged in contact inside a support carrier, wherein the plurality of structures are produced by changing contact lengths of said first cell aggregates and said second cell aggregate, wherein said first cell aggregates comprise mesenchymal cells and said second cell aggregates comprise epithelial cells, wherein at least one of the mesenchymal cell and the epithelial cell is derived from a tooth germ, wherein said first cell aggregate and said second cell aggregate are cell masses; a step of culturing each of the plurality of structures inside the support carrier, such that teeth are produced; and a step of measuring the number of teeth produced in the preceding step and determining the maximum contact length between a first cell aggregate and a second cell aggregate that is required for obtaining a single tooth.

14. The method according to claim 12, wherein both the mesenchymal cell and the epithelial cell are derived from a tooth germ.

* * * * *